US007497950B2

(12) United States Patent
Sirkar et al.

(10) Patent No.: US 7,497,950 B2
(45) Date of Patent: Mar. 3, 2009

(54) HIGHLY SELECTIVE MEMBRANE SYSTEMS AND METHODS FOR PROTEIN ULTRAFILTRATION

(75) Inventors: Kamalesh Sirkar, Bridgewater, NJ (US); Meredith Feins, River Vale, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 417 days.

(21) Appl. No.: 11/125,635

(22) Filed: May 10, 2005

(65) Prior Publication Data

US 2005/0255227 A1 Nov. 17, 2005

Related U.S. Application Data

(60) Provisional application No. 60/571,097, filed on May 14, 2004.

(51) Int. Cl.
*B01D 61/14* (2006.01)
*B01D 61/18* (2006.01)

(52) U.S. Cl. ............... 210/651; 210/645; 210/321.64; 210/650; 422/101

(58) Field of Classification Search .................. None
See application file for complete search history.

(56) References Cited

U.S. PATENT DOCUMENTS 4,895,806 A * 1/1990 Le et al. .................. 435/293.1

5,256,294 A * 10/1993 van Reis ..................... 210/637
2003/0089664 A1* 5/2003 Phillips ...................... 210/660
2005/0126980 A1* 6/2005 Pahl et al. ............... 210/321.72

FOREIGN PATENT DOCUMENTS

WO WO 01/49401 A1 * 12/2001

OTHER PUBLICATIONS

Boyd, et al., Sieving Characteristics of Multilayer Ultrafiltration Membranes, Journal of Membrane Science, 131, 1997, pp. 155-165.
Cheang, et al., A Two-Stage Ultrafiltration Process For Fractionation of Whey Protein Isolate, Journal of Membrane Science, 231, 2004, pp. 159-167.
PCT International Search Report dated Oct. 25, 2005.

(Continued)

*Primary Examiner*—Krishnan S Menon
(74) *Attorney, Agent, or Firm*—McCarter & English, LLP

(57) ABSTRACT

A new ultrafiltration technique based on a multimembrane stack has been developed to fractionate solutes closer in size than conventionally possible. The technique is illustrated here by obtaining a pure protein product from a binary protein mixture. By employing membranes in series without any gaskets or spacers in-between, ultrafiltration is carried out to separate two proteins relatively close in molecular weight or size. Flat regenerated cellulose membranes, polyethersulfone membranes or the like, of at least substantially the same molecular weight cutoff (MWCO) are stacked together in the desired number, and ultrafiltration takes place. The membrane rejection of a protein is amplified with each additional membrane, ultimately resulting in a completely rejected species. Complete purification of the more permeable protein is achieved regardless of the physicochemical condition which may be optimal or suboptimal for selective separation by a single membrane.

9 Claims, 13 Drawing Sheets

OTHER PUBLICATIONS

Saksena, et al., Effect of Solution pH and Ionic Strength on the Separation of Albumin from Immunoglobulins (IgG) by Selective Filtration, Biotechnology and Bioengineering, 1994, vol. 43, pp. 960-968.

Kurnik, et al., Buffer Exchange Using Size Exclusion Chromatography, Countercurrent Dialysis, and Tangential flow filtration: Models, Development, and Industrial Application, Biotechnology and Bioengineering, 1995, vol. 45, pp. 149-157.

Burba, et al., Membrane Filtration Studies of Aquatic Humic substances and Their metal Species: A Concise Overview, Talanta 45, 1998, pp. 977-988.

Van Eijndhoven, et al., Protein Fractionation Using Electrostatic Interactions in Membrane Filtration, Biotechnology and Bioengineering, 1995, vol. 48, pp. 406-414.

Cherkasov, The Resolving Power of Ultrafiltration, Journal of Membrane Science, 1996 vol. 110, pp. 79-82.

Kim, et al., Evaluation of Electroosmosis and Streaming Potential For Measurement of electric Charges of Polymeric Membranes, Journal of Membrane Science, 1996, vol. 116, pp. 149-159.

Boyd, et al. Sieving Characteristics of Multilayer Ultrafiltration Membranes, Journal of Membrane Science, 1997, vol. 131, pp. 155-165.

Prazeres, A Theoretical Analogy Between Multistage Ultrafiltration and Size-Exclusion Chromatography, Chemical Engineering Science, 1997, vol. 52, No. 6, pp. 953-960.

Van Reis, et al., High Performance Tangential Flow Filtration, Biotechnology and Bioengineering, 1997, vol. 56, pp. 71-82.

Nystrom, et al., Fractionation of Model Proteins Using Their Physiochemical Properties, Colloids and Surfaces, A: Physicochemical and Engineering Aspects, 1998, vol. 138, pp. 185-205.

Burns, et al., Buffer Effects on the Zeta Potential of Ultrafiltration Membranes, Journal of Membrane Science, 2000, vol. 172, pp. 39-48.

Ghosh, Novel Cascade Ultrafiltration Configuration For Continuous, High-Resolution Protein-Protein Fractionation: A Simulation Study, Journal of Membrane Science, 2003, vol. 226, pp. 85-99.

* cited by examiner

Experimental rejection behaviors for one membrane system at three different pressures. Batch ultrafiltration of system 1 (1.0 mg/ml β-lactoglobulin and 0.2 mg/ml myoglobin, pH 7.3; 3.5, 5.0, and 10.0 psig)

Experimental and calculated rejection behaviors of myoglobin
for 2 and 3 membrane systems. Batch ultrafiltration of system 1
(1.0 mg/ml β-lactoglobulin and 0.2 mg/ml myoglobin, pH 7.3, 10 psig)

Experimental and calculated rejection behaviors of β-lactoglobulin for 2 and 3 membrane systems. Batch ultrafiltration of system 1 (1.0 mg/ml β-lactoglobulin and 0.2 mg/ml myoglobin, pH 7.3, 10 psig)

HIGHLY SELECTIVE MEMBRANE SYSTEMS AND METHODS FOR PROTEIN ULTRAFILTRATION

CROSS-REFERENCE TO RELATED APPLICATIONS

The present application claims the benefit of a provisional patent application entitled "Highly Selective Membrane Systems and Methods for Use in Protein Ultrafiltration," which was filed on May 14, 2004 and assigned Ser. No. 60/571,097. The entire contents of the foregoing provisional patent application are hereby incorporated by reference.

BACKGROUND

1. Technical Field

The present disclosure relates to systems and methods for obtaining protein(s). More particularly, the present disclosure relates to systems and methods for obtaining protein(s) from a protein mixture, e.g., a binary protein mixture, by utilizing membranes. The membranes may be advantageously aligned in series. According to the disclosed systems and methods, ultrafiltration may be carried out on at least two proteins of substantially the same molecular weight simultaneously. In exemplary embodiments of the present disclosure, flat regenerated cellulose membranes and/or polyethersulfone membranes that possess substantially the same molecular weight cutoff (MWCO) are stacked together in a desired number to effectuate ultrafiltration, the efficacy of such stacking being further assisted by optimization of the feed conditions, membrane selection and/or membrane charge conditions to enhance/maximize selectivity.

2. Background of Related Art

Downstream protein purification from a fermentation broth is complicated by the presence of a large number of impurities, pyrogens, and viruses. Because a completely purified bioproduct is generally desired, many purification processes have been investigated, including chromatography, membrane adsorption or membrane chromatography, and ultrafiltration [Harrison R, *Protein purification process engineering*, New York: Marcel Dekker, 1994]. These techniques are successfully used in industry to purify biomolecules; however, the development of techniques that increase the selectivity and reduce the cost are highly desirable, making them the current focus of research.

Chromatographic processes achieve very high selectivities based on solute interaction with specific beads [Scopes R K., *Protein purification principles and practice*, 3rd Ed., New York: Springer Verlag, 1994]. In this process, separation is limited by diffusion in and out of the resin. Recent development of gigaporous particles facilitating convective flow through the particles is expected to mitigate this problem [Pfeiffer J F, Chen J C, Hsu J T, *Permeability of gigaporous particles*. AIChE J 42:932-939, 1996]. However, the buffer volume employed is very high. Scaleup is problematic and column chromatography is costly. In membrane adsorption processes, ligands are grafted on to the surface of pores in microfiltration membranes; biomolecule adsorption is achieved during convection through the membrane pores [Thömmes J, Kula M R, *Membrane chromatography—an integrated concept in the downstream processing of proteins*, Biotechnol Prog 11: 357-367, 1995]. This process is attractive because of the large pore size in microfiltration membranes, which allows much easier and convective access to the binding sites rather than diffusion in beads packed in chromatography columns. The ligand utilization is orders of magnitude higher. But it is not a steady state process. Overall capacity is low, therefore multiple cycles are needed.

The techniques mentioned above require specially designed adsorbents and unusual operating conditions. For example, membrane adsorption processes employ rapid cyclic procedures consisting of many cycles in which each cycle requires an adsorption, elution, and regeneration step. In addition, column chromatography is very costly. Membrane chromatographic processes have problems with dispersion in current device designs [Gebauer K H, Thommes J, Kula M R, *Plasma protein fractionation with advanced membrane adsorbents*, Biotechnol Bioeng 54:181-189, 1997], binding capacities comparable with beads have not been achieved [Sarfert F T, Etzel M R, *Mass transfer limitations in protein separations using ion-exchange membranes*, J Chromatogr A 764:3-20, 1997].

Ultrafiltration has traditionally been used for size-based separation of protein mixtures where the ratio of the protein molecular masses is at least around 7-10 [Cherkasov A N, Polotsky A E, *The resolving power of ultrafiltration*, J Membr Sci 110:79-82, 1996]. In order to achieve better purification of similarly sized biomolecules, significant research has taken place focusing on "fine tuning" the operating and physicochemical conditions to achieve higher selectivity [Saksena S, Zydney A L, *Effect of solution pH and ionic strength on the separation of albumin from immunoglobulins (IgG) by selective ultrafiltration*, Biotechnol Bioeng 43:960-968, 1994; Eijndhoven R H, Saksena S, Zydney A L, *Protein fractionation using electrostatic interactions in membrane filtration*, Biotechnol Bioeng 48:406-414, 1995; Nystrom M, Aimar P, Luque S, Kulovaara M, Metsamuuronen S, *Fractionation of Model Proteins using their Physiochemical Properties. Colloids and Surfaces A*, Physiochemical and Engineering Aspects 138:185-205, 1998]. This allows the protein size differential to be exploited further due to the increased or decreased hydrodynamic radius that results from buffer conditions (i.e., ionic strength and pH). Some have employed these concepts along with a preliminarily determined optimal operating flux or transmembrane pressure drop to develop a technique called high-performance tangential flow filtration (HPTFF) [Van Reis R, Gadam S, Frautschy L N, Orlando S, Goodrich E M, Saksena S, Kuriyel R, Simpson C M, Pearl S, Zydney A L, *High Performance Tangential Flow Filtration*, Biotechnol Bioeng 56:71-82, 1997]. These HPTFF units can also be used in series to improve separation.

Others have examined theoretically an analogy between multistage ultrafiltration and size-exclusion chromatography [Prazeres D M F, *A theoretical analogy between multistage ultrafiltration and size-exclusion chromatography*, Chem Eng Sci 52:953-960, 1997]. A large stack of membranes was analyzed and compared to column chromatography for fractionation of solutes according to their size. It was suggested that such a multistage ultrafiltration-based chromatographic process behaves in an opposite fashion when compared to size-exclusion chromatography by eluting solutes in increasing order of their size. In this analysis, all of the solutes pass through the column at different rates depending on their size. No experimental data has been provided. The number of ultrafiltration membranes to be used in a stack could also number as high as 2500.

Sequentially-staged ultrafiltration membrane processes have been studied to separate aquatic humic substances [Burba P, Aster B, Nifant'eva T, Shkivnev V, Spivakov, B, *Membrane filtration studies of aquatic humic substances and their metal species: a concise overview Part* 1. *Analytical fractionation by means of sequential-stage ultrafiltration*, Talanta 45: 977-988, 1998]. Tangential flow-based filtration takes place through ultrafiltration membranes that are placed in series in different compartments with decreasing molecular weight cut offs (MWCOs) and allowed to collect in a reservoir after each stage. The flow rate across each membrane is controlled by a multi-channel pump.

Ultrafiltration, with optimized conditions, only improves the selectivities, not always resulting in a pure product. HPTFF requires extensive system optimization. Sequentially-staged ultrafiltration requires an extraordinarily large amount of equipment due to the multiple stages and pumps and has not received significant interest. This is because conventional multistage ultrafiltration is grossly inefficient in fractionating/purifying proteins having molecular weight ratios less than five [Ghosh, R, *Novel cascade ultrafiltration configuration for continuous high-Resolution protein-protein fractionation: a simulation study*, J Membr Sci 226:85-99, 2003]. Novel cascade configurations in separate devices with individual pumps have therefore been investigated to achieve protein purification by Ghosh [2003], who numerically illustrates such a three-stage process for protein fractionation using two proteins whose apparent sieving coefficients are 0.5 (preferentially transmitted) and 0.01 (preferentially retained).

In general, the advantages of membrane devices over chromatographic systems are lower capital cost and steady-state operation, which allow efficient transfer to large-scale operation. Ultrafiltration has become the preferred method of choice for protein concentration and buffer exchange, replacing size-exclusion chromatography [Kurnik R T, Yu A W, Blank G S, Burton A R, Smith D, Athalye A M, Van Reis R, *Buffer exchange using size exclusion chromatography, countercurrent dialysis, and tangential flow filtration: models, development, and industrial application*, Biotechnol Bioeng 45:149-157, 1995]. Changing the physicochemical environment as well as chemical modification of membranes have been extensively studied, and allow high-resolution protein separations [Saksena S, Zydney A L., *Effect of solution pH and ionic strength on the separation of albumin from immunoglobulins (IgG) by selective ultrafiltration*, Biotechnol Bioeng 43:960-968, 1994; Eijndhoven R H, Saksena S, Zydney A L., *Protein fractionation using electrostatic interactions in membrane filtration*, Biotechnol Bioeng 48:406-414, 1995; Nystrom M, Aimar P, Luque S, Kulovaara M, Metsamuuronen S., *Fractionation of Model Proteins using their Physiochemical Properties. Colloids and Surfaces A*, Physiochemical and Engineering Aspects 138:185-205, 1998]. Laboratory as well as large-scale UF devices employ a simple flat membrane conventionally in a single stage [Kulkarni S S, Funk E W, Li N N, *Ultrafiltration, in* Ho W S and Sirkar K K editors, *Membrane Handbook*, Boston: Kluwer Academic Publishers, pp 393-453, 2001]. But by using a cascade operation in one stage, a single-staged optimized separation can be exploited to achieve very high selectivities that are characteristic of multiple stages that, until now, were only achievable using conventional column chromatographic methods. One device that yields a completely purified biomolecule by completely rejecting the unwanted species is highly desirable.

Typical membrane cascade operations are performed by transferring the permeate from one membrane device into a second device as the feed. In this research, multiple flat membranes are sandwiched together and housed in one device [Kulkarni S S, Funk E W, Li N N, *Ultrafiltration, in* Ho W S and Sirkar K K editors, *Membrane Handbook*, Boston: Kluwer Academic Publishers, pp 393-453, 2001]. The permeate from the first membrane is the feed for the second membrane, and the permeate from the second membrane is the feed for the third membrane, etc. Therefore, the rejection of one protein through one membrane will be substantially increased with each additional membrane eventually resulting in, on an overall basis, essentially complete rejection of one species. By using a membrane stack, e.g., a stack of 3, 4, or 5 membranes, it is possible to achieve an essentially completely pure product. We may also compensate for the solvent flux loss with each added membrane while still maintaining the effectiveness of the design by raising the feed solution pressure. However, the volume of the feed solution being imposed on each membrane, except for the first one, is very small.

Limited studies have been made where two asymmetric Omega 30K and 50K MWCO membranes were used in a sandwich, either with their support substructures together (i.e., the skin layers on the two outer surfaces) or with the skin layers together (i.e., with the porous substructures at the upstream and downstream surfaces) [Boyd R F, Zydney A L, *Sieving characteristics of multilayer ultrafiltration membranes*, J Membr Sci 131:155-165, 1997].

Despite efforts to date, a need remains for enhanced separation systems and methods, particularly separation systems and methods that are effective to separate proteins from protein mixtures in a cost effective and efficacious manner. Moreover, separation systems and methods are needed that can be effectively employed in protein systems wherein the ratio of the protein molecular mass is less than about 7 to about 10. These and other objectives are advantageously satisfied according to the disclosed systems and methods, as described herein.

SUMMARY OF THE DISCLOSURE

Current ultrafiltration (UF) membranes may be used for size-based separation of protein mixtures only when the ratio of the protein molecular masses is at least around about 7 to about 10. By altering the operating and physiochemical conditions (e.g., pH, ionic strength) and the membrane charge, the selectivity can be considerably improved. However, the level of purification attained by chromatography is generally never achieved in conventional UF-based separation of protein mixtures. The systems and methods of the present disclosure provide for flat UF membranes, e.g., conventional UF membranes, to be stacked one over the other to a suitable level (e.g., about 3 to about 5 or more). By effectuating ultrafiltration of a feedstock through a stacked membrane apparatus/assembly according to the present disclosure, the system and method of the present disclosure advantageously provides an essentially complete rejection of a more rejected protein. The membrane stack/composite substantially reduces the flux for a given level of applied pressure difference and advantageously enables the flux to be restored by raising the feed pressure, as appropriate. The membrane stack/composite may be easily cleaned in situ and repeatedly used. Protein species whose molecular weights differ by as little as about 1.03 may be separated and one species obtained in pure form.

Thus, the present disclosure is directed to a system and method for obtaining protein from a protein mixture, e.g., a binary protein mixture, by utilizing membranes. The membranes are advantageously stacked in series. In an exemplary embodiment of the present disclosure, the membranes are stacked without any gaskets or spacers therebetween. In alternative exemplary embodiments, gasket(s) and/or spacer(s) may be provided between one or more adjacent pairs of membranes, provided appropriate design steps are undertaken to ensure proper sealing between adjacent membranes. Thus, for example, the membranes, gaskets (if present) and spacers (if present) are sized, configured and fabricated from materials that sealingly interact with each other. According to this system design, ultrafiltration may be carried out on at least two proteins of substantially the same molecular weight simultaneously. Flat UF membranes, e.g., regenerated cellulose membranes and/or polyethersulfone membranes, that possess the same or substantially the same MWCO (as described below) may be stacked together in a desired number, whereby ultrafiltration occurs. Alternative materials may be employed in fabricating membranes for use according to the present disclosure. For example, UF membranes may be fabricated from alternative materials, such as polysulfone, polyvinylidenefluoride, polyacrylonitrile, cellulose acetate, cellulose triacetate, cellulose nitrate, polyimides, polyamides, or the like. Performance of the disclosed stack/composite may be further assisted/enhanced through optimization of the feed conditions, membrane selection and/or membrane charge selection to maximize selectivity, as described herein.

The technique of the present disclosure provides an improvement over existing techniques. The disclosed system/method provide membranes with MWCO's that are smaller than those currently commercially available. Presently, when performing ultrafiltration, the use of smaller MWCO membranes to obtain complete rejection of a solute causes a decrease in the solvent flux due to the reduction in pore size. In distinct contrast relative to prior art systems, the system/method of the present disclosure advantageously overcomes this problem by developing/deploying customized MWCO membranes with less flux reduction than would be found by changing to a smaller MWCO membrane.

Thus, the system and method of the present disclosure advantageously provides a pure or at least substantially pure product, e.g., the observed rejection characteristics for a single membrane have been demonstrated to be amplified in a multi-membrane stack. Still further, unlike certain known techniques (e.g., chromatography), systems/methods in accordance with the present disclosure are advantageously continuous, scalable, easily operated, efficient and relatively economic.

In short, the disclosed system configuration is essentially different from prior art systems, e.g., the system disclosed by Boyd and Zydney [1997]. Although the systems of the present disclosure use the same membrane-based composite(s), the stack/composite configuration of the present disclosure, i.e., skin-backing-skin-backing-skin-backing, enhances performance and provides substantial processing advantages. According to an exemplary embodiment of the present disclosure, three membranes correspond to the minimum number of membranes in a composite membrane configuration.

Separation of proteins utilizing internally staged ultrafiltration membranes has thus been demonstrated as an alternative to current purification processes. In exemplary embodiments of the present disclosure, by using 1, 2-, and 3-membrane composites, it has been shown that one pure protein can be obtained in the permeate for the systems of 1) myoglobin (Mb) and β-lactoglobulin (β-LG), 2) alpha-lactalbumin (α-LA) and myoglobin (Mb), and 3) hemoglobin (Hb) and bovine serum albumin (BSA). This performance was achieved by effectively narrowing the pore size distribution of commercially available membranes and allowing the de facto development of unique new membranes with alternative molecular weight cutoffs (MWCOs). The flux loss was minimal compared to the flux loss that would have been encountered if one used the next smaller MWCO membrane available. It is expected that investigations on larger pore size membranes, larger protein molecular weights, and closer molecular weight ratios may be useful in establishing the applicability of the disclosed systems and methods to various downstream mixtures. The membrane systems and techniques of the present disclosure may also be used in the separation and purification of other biopolymers, including for example polysaccharides.

Multi-component separations are another advantageous application for the multi-membrane composite systems and methods of the present disclosure. Indeed, many systems requiring separation contain more than two proteins. For example, in a three species/protein system, by operating at or about the pI (isoelectric point) of one of the species/proteins as a first separation step, one can achieve one pure species/protein component in the permeate using a multi-membrane system of the present disclosure, leaving the remainder of the multi-component feed in the retentate. By implementing a further pH adjustment, i.e., to a new pH value that equals (or approximates) the pI of a second species/protein of interest in the multi-component system, one can recover a second purified species/protein, with the third species/protein left in the retentate after the second separation stage.

To further illustrate the disclosed multi-component separation system of the present disclosure, reference is made to an exemplary multi-component mixture of whey proteins. Whey protein isolate/concentrate contains three different proteins among the lower molecular weight proteins, namely: α-lactalbumin (α-LA), β-lactoglobulin (β-LG), and bovine serum albumin (BSA). Conventional ultrafiltration cannot effectively purify all three proteins via two-stage separation; see for example, B. Cheang and A. L. Zydney, "A two-stage ultrafiltration process for fractionation of whey protein isolate," J. of Membrane Science, vol. 231, pages 159-167 (2004). As described in the foregoing publication, the separated products were not pure. Therefore, a more effective alternative is attractive. By utilizing the flat multi-membrane composite of appropriate UF membranes, as disclosed herein, first at a pH equal to approximately 4.35 (which is the pI of α-lactalbumin) followed by adjusting the pH to about 5.5 (which is the pI of β-lactoglobulin), complete separation may be achieved leaving pure bovine serum albumin in the retentate after the second separation stage.

In accordance with the present disclosure, multiple numbers of the same membrane may be stacked/sandwiched together without any artificial spacer, gaskets, or adhesives in between to achieve the purest product. Commercially available flat ultrafiltration membranes of regenerated cellulose and polyethersulfone, e.g., of about 30,000 or 100,000 MWCO, may be employed. For specific implementations of the disclosed systems and methods, membranes may be selected based on MWCO or pore size compared with the size of the targeted molecule/biomolecule to be purified. Physicochemical conditions (i.e., pH, ionic strength) may also be selected based on the characteristics of the target molecule/biomolecule in order to achieve the highest selectivities. Additionally, non-optimized buffer conditions may also be employed. Optimized or non-optimized buffer typically flows through the ultrafiltration cell in constant diafiltration mode. A feed solution may be introduced to the disclosed system/method in a batch mode or a continuous mode; alternatively, the feed solution may be introduced as a pulse input. In an exemplary embodiment of the present disclosure, the feed solution may be a binary protein mixture.

Thus, according to an exemplary implementation of the present disclosure, the feed solution may be a binary protein mixture. By way of example only, a mixture of hemoglobin (MW 64677) and bovine serum albumin (MW 66430) may be effectively separated using the systems and methods of the present disclosure. Of note, the molecular weight ratio of the hemoglobin/bovine serum albumin system is 1.03. Binary protein mixtures may also be employed according to the disclosed system/process. In situ cleaning of the membrane stack/composite has also been implemented to establish the extent to which the membranes retain their separation characteristics for many production batches without significant downtime to the overall process.

Membrane stacks, containing different numbers of membranes, can be sealed together around the perimeter and sold/used as one unit. Many different types of commercially available flat membranes can be utilized. Functionalized membranes that contain specific ligands or stacks of membranes that contain ligands in-between the membranes for enhanced separation are also a design option according to the present disclosure. These units are attractive because they are disposable, inexpensive, and compact. There are endless possible applications of the disclosed membrane stacks/composites of the present disclosure, from bench to large scale. By utilizing these membrane stacks, separation of mixtures can be achieved that until now were only possible using costly chromatographic methods, high volume and equipment cascades, or system specific membrane devices.

These and other structural, functional and operating advantages of the disclosed ultrafiltration membrane systems will be more readily apparent from the detailed description which follows, particularly when reviewed in connection with the figures appended hereto.

BRIEF DESCRIPTION OF THE FIGURES

So that those having ordinary skill in the art to which the present disclosure pertains will more readily understand the disclosure described herein and methods, processes and systems for implementation thereof, exemplary aspects thereof will be discussed in association with the appended figures, wherein.

DETAILED DESCRIPTION OF EXEMPLARY EMBODIMENT(S)

Figure 1:
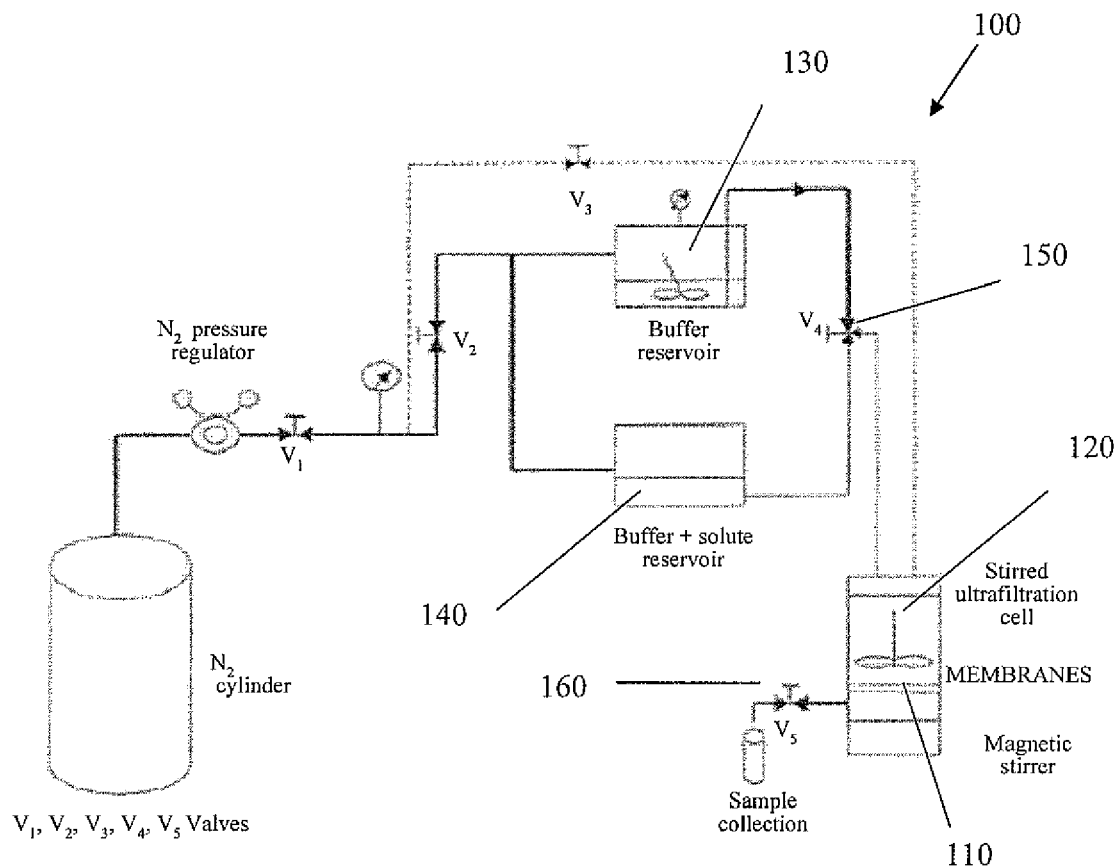
FIG. 1 is a schematic diagram of an experimental set-up for ultrafiltration in accordance with an exemplary aspect of the present disclosure.

The present disclosure provides an advantageous system and method to effectively fractionate molecules/biomolecules by stacking flat UF membranes of the same or substantially the same MWCO in series. As used herein, membranes that have substantially the same MWCO generally have MWCOs that differ by no more than about 10 to 20% for membranes having a MWCO of greater than about 50,000. For membranes having a MWCO less than about 50,000, such membranes may be characterized as having substantially the same MWCO if the MWCO of adjacent membranes differ by no more than about 25 to 40%.

In accordance with observations, experimentally obtained results demonstrate that rejection characteristics observed for a single membrane can be substantially amplified in a multi-membrane stack which, in turn, can result in a pure product in buffer and membrane optimized and non-optimized systems. Further, similarly advantageous results have been observed in batch UF, continuous UF, as well as pulse-fed UF systems according to the present disclosure. Still further, for a multi-membrane stack of, for example, three or more membranes to succeed in producing a pure protein in the permeate, the rejection by a single UF membrane generally must generally be substantial. Thus, optimization of the pH, ionic strength and/or other operating parameters and/or selecting membrane(s)/membrane charge level(s) may be important to achieving the goal of obtaining one pure protein in the permeate.

The operating pressure may be increased to compensate for solvent flux loss encountered with the addition of each new membrane in the stack. It has also been shown that the solvent flux is constant over a period of time in the range from about 50 minutes to about 15 hours. In situ cleaning may be carried out to allow cleaning of the stack without disrupting the process and allowing pure water flux to be essentially completely recovered and cyclic processes to be utilized effectively.

The technique in accordance with the present disclosure may be suitable for use in any of a variety of systems, such as, for example, systems containing complex mixtures. A host of multi-component separations may be advantageously achieved using the disclosed multi-membrane systems and techniques described herein. For example, in a three species/protein system, sequential separation may be achieved through variations in pH conditions based on the pI properties of the individual species/proteins included in the multi-component system. Thus, by operating at or about the pI (isoelectric point) of one of the species/proteins, a first pure species/protein component may be obtained in the permeate, leaving the remainder of the multi-component feed in the retentate. By implementing a further pH adjustment, i.e., to a new pH value that equals (or approximates) the pI of a second species/protein, a second purified species/protein may be recovered, with the third species/protein left in the retentate after the second separation stage. As noted above, an exemplary application of the disclosed three species/protein separation process described herein involves separation of individual proteins from whey protein, thereby enabling separate recovery of lower molecular weight proteins, e.g., α-lactalbumin (α-LA), β-lactoglobulin (β-LG), and bovine serum albumin (BSA). By utilizing the disclosed flat multi-membrane composite of appropriate UF membranes, first at a pH equal to approximately 4.35 (which is the pI of α-lactalbumin) followed by pH adjustment to about 5.5 (which is the pI of β-lactoglobulin), complete separation may be achieved, leaving pure bovine serum albumin (BSA) in the retentate after the second separation stage.

The system/method of the present disclosure preferably has significant applicability for separation of many different types of solute mixtures. By keeping the cost and size low, the system/method of the present disclosure may be attractive to all types of researchers and/or manufacturers. Further, utilizing commercially available membranes in constructing the disclosed stacks/composites can allow the user to be familiar with the membrane characteristics and reduce the cost of membrane fabrication. Applications for the systems/methods of the present disclosure may be varied and the associated investment quite low.

To illustrate the efficiency and efficacy of the disclosed system/method for obtaining protein from a binary protein mixture by utilizing membranes in series, systems that included the following proteins were tested:

α-lactalbumin (α-LA, MW 14175; Vanaman, T C, Brew K, Hill R L, *The complete amino acid sequence of bovine alpha-lactalbumin*, The Journal of Biological Chemistry 245: 4570-82, 1970), myoglobin (Mb, MW 17566; Darbre P D, Romero-Herrera A E, Lehmann H, *Comparison of the myoglobin of the zebra (Equus burchelli) with that of the horse (Equus caballus)*, Biochemica et Biophysica Acta 393:201-204, 1975), and β-lactoglobulin (β-LG, MW 35500; Townend, R., Weinberger, L., and Timasheff, S N, *Molecular Interactions in β-Lactoglobulin. I, The Electrophoretic Heterogeneity of β-Lactoglobulin Close to its Isoelectric Point*, J Am Chern Soc, 1960, 82, 3157, 1960).

All of the tested proteins were purchased from Sigma (St. Louis, Mo.).

The pI values for α-LA, Mb, and β-LG are respectively 4.2-4.5 (Kronman M J, Andreotti R E. 1964. Inter- and Intramolecular Interactions of α-Lactalbumin. I, *The Apparent Heterogeneity at Acid pH. Biochemistry* 3:1145-1151, 1964), 7.3 (Radola B J, *Isoelectric focusing in layers of granulated gels. I. Thin-layer isoelectric focusing of proteins*, Biochimica et Biophysica Acta 295:412-428, 1973), and 5.3 (Kaplan L J, Foster J F, *Isoelectric focusing behavior of bovine plasma albumin, mercaptalbumin, and beta-lactoglobulins A and B*, Biochemistry 10:630-636, 1971). 20 mM Tris-HCL buffer at pH 7.3 and 20 mM citric acid buffer at pH 6.0 and 4.35 were used as buffers. Two binary mixtures were studied: system 1 containing myoglobin and β-lactoglobulin; system 2 containing α-lactalbumin and myoglobin.

In accordance with an illustrative aspect of the present disclosure, protein solutions were prepared by dissolving the desired protein in the appropriate buffer solution at room temperature. Buffer solutions were prefiltered through a 0.45 μm pore size Durapore membrane (Millipore, Bedford, Mass.) prior to use. The protein solutions were then prefiltered through 0.45 μm pore size Durapore membranes (Millipore) to remove any undissolved proteins and large particulates. Protein solutions were stored at 4° C. and used within 24 hours in order to ensure no bacterial contamination. The protein concentrations in the mixture were determined by the dual-wavelength method using a Hitachi U-2000 (Danbury, Conn.) UV-VIS spectrophotometer at 410 nm and 280 nm.

Referring to FIG. 1, an experimental set-up 100 in accordance with an illustrative aspect of the present disclosure is shown. The first experiment employed regenerated cellulose flat membrane disks (YM30, MWCO 30,000, diameter 76 mm) 110 from Millipore (Bedford, Mass.). Prior to use, these membranes were soaked in buffer solution for 1 hour. The filtration experiment was conducted using a 76 mm stirred ultrafiltration cell (model 8400, Amicon Corporation) 120 and two solvent reservoirs 130, 140. Multiple experiments were performed using at least one buffer reservoir 130 of stainless steel filled with a pure specific buffer of an appropriate pH while another acrylic reservoir 140 contained a feed solution, cleaning solution, or was left empty to be used for steady state experiments. All of the experiments were batch ultrafiltration experiments with fresh buffer replacing the lost solvent volume.

In accordance with another aspect of the present disclosure, pulse experiments were also performed by placing a highly concentrated feed solution (that was prepared as to have the desired final concentration in the ultrafiltration cell) in the second acrylic reservoir 140, while appropriate buffer was placed in the cell 120. The buffer flow rate was monitored. By knowing the flow rate, the injection time for a specific volume of feed was calculated and an "injection" was made by turning a three way valve 150. By contrast, in experiments started with a batch feed, the ultrafiltration cell 120 was filled directly with the feed solution and the second reservoir 140 was empty; buffer continued to flow from the first reservoir 130.

In preliminary experiments, single membrane studies were conducted with a binary protein mixture. These preliminary experiments were operated at different pressures to explore the rejection characteristic encountered in-between the membrane stack where concentrations cannot be measured directly. More membranes were added to illustrate the changing rejection behavior. Membranes of a determined number were stacked together without any adhesive or spacer in-between them. Fractions were collected at timed intervals and the permeate flow rate was measured using timed collections. All experiments were conducted at constant pressure and were performed at room temperature (22±2° C.).

Occasionally after ultrafiltration experiments were completed, the membranes were soaked in deionized water overnight (prior to cleaning). The water solution was then analyzed to measure the amount of protein that was desorbed from the membrane. The cleaning was conducted in two ways: in situ or off-line.

In situ cleaning was done by allowing the feed solution to completely exit the ultrafiltration cell 120. The second reservoir 140 was filled with 0.1 M NaOH and this solution was allowed to enter the stirred cell 120 and permeate through the membranes 110. Then, an exit valve 160 was closed and the cleaning solution was allowed to soak in the membranes. The solution then exited the cell 120 via the membranes with a total time of exposure being 30 minutes (which is according to the manufacturer's specifications). Warm water (~70° C.) from the second reservoir 140 was then allowed to pass through the system for one hour. The warm water was then switched to ambient temperature water and the pure water flux was monitored. The integrity of the membrane is maintained if this flux is within 95% of the virgin membrane's pure water flux. The membranes were stored in 10% ethanol/water solution at 4° C. Whereas, off-line cleaning was accomplished by disassembling the apparatus and briefly rinsing the membranes with tap water. Then the membranes were allowed to soak in 0.1 M NaOH at room temperature for 30 minutes.

Results and Discussion

The solute rejection $R_1$ for the first membrane as well as a single membrane for a solute is given by:

$$R_1 = 1 - C_{p1}/C_{f1} \tag{1}$$

where $C_{p1}$ is the solute concentration on the permeate side of membrane 1 and $C_{f1}$ is the solute concentration on the feed side of membrane 1 exposed to the feed solution. The concentrations of solutes in the retentate are changing over time due to the addition of fresh buffer and loss of solutes due to ultrafiltration; therefore, a mass balance is used to calculate $C_{f1}$ for every solute and for every data point. Rejection values can be calculated for a system of multiple membranes by assuming that the feed to the second membrane is the permeate from the previous membrane, etc. The rejection for a two-membrane system can be calculated from rearranging equation 1 and assuming a constant rejection value valid for a single membrane system; the feed to the second membrane $C_{f2}$ is $C_{p1}$ the permeate from the first membrane. Correspondingly, the feed to the third membrane, $C_{f3}$ is really $C_{p2}$, which is the concentration of the permeate from membrane 2. Consequently:

$$C_{p1} = (1-R_1)C_{f1} \tag{2a}$$

$$C_{p2} = (1-R_1)C_{p1} \tag{2b}$$

$$C_{p2} = (1-R_1)^2 C_{f1}; \quad C_{p2}/C_{f1} = (1-R_1)^2 \tag{2c}$$

$$C_{p3} = (1-R_1)C_{p2} = (1-R_1)^2 C_{p1} = (1-R_1)^3 C_{f1} \tag{2d}$$

$$C_{p3}/C_{f1} = (1-R_1)^3 \tag{2e}$$

The overall rejections $R_2$, $R_3$ respectively for the systems of two membranes and three membranes in series are defined as:

$$R_2 = 1 - C_{p2}/C_{f1} \tag{3}$$

$$R_3 = 1 - C_{p3}/C_{f1} \tag{4}$$

Therefore, $R_2$ and $R_3$ may be calculated respectively by the following equations $$R_2 = 1 - (1-R_1)^2 \tag{5}$$

$$R_3 = 1 - (1-R_1)^3 \tag{6}$$

These relationships show how high the rejection can be when it is amplified with each additional membrane.

Notation $C_{f1}$ concentration of solute on the feed side of membrane 1, μg/ml $C_{f2}$ concentration of solute on the feed side of membrane 2, μg/ml $C_{f3}$ concentration of solute on the feed side of membrane 3, μg/ml $C_{p1}$ concentration of solute on the permeate side of membrane 1, μg/ml $C_{p2}$ concentration of solute on the permeate side of membrane 2, μg/ml $C_{p3}$ concentration of solute on the permeate side of membrane 3, μg/ml $R_1$ rejection of solute through membrane 1

$R_2$ rejection of solute through a stack of membranes 1 and 2

$R_3$ rejection of solute through a stack of membranes 1, 2 and 3

Figure 20:
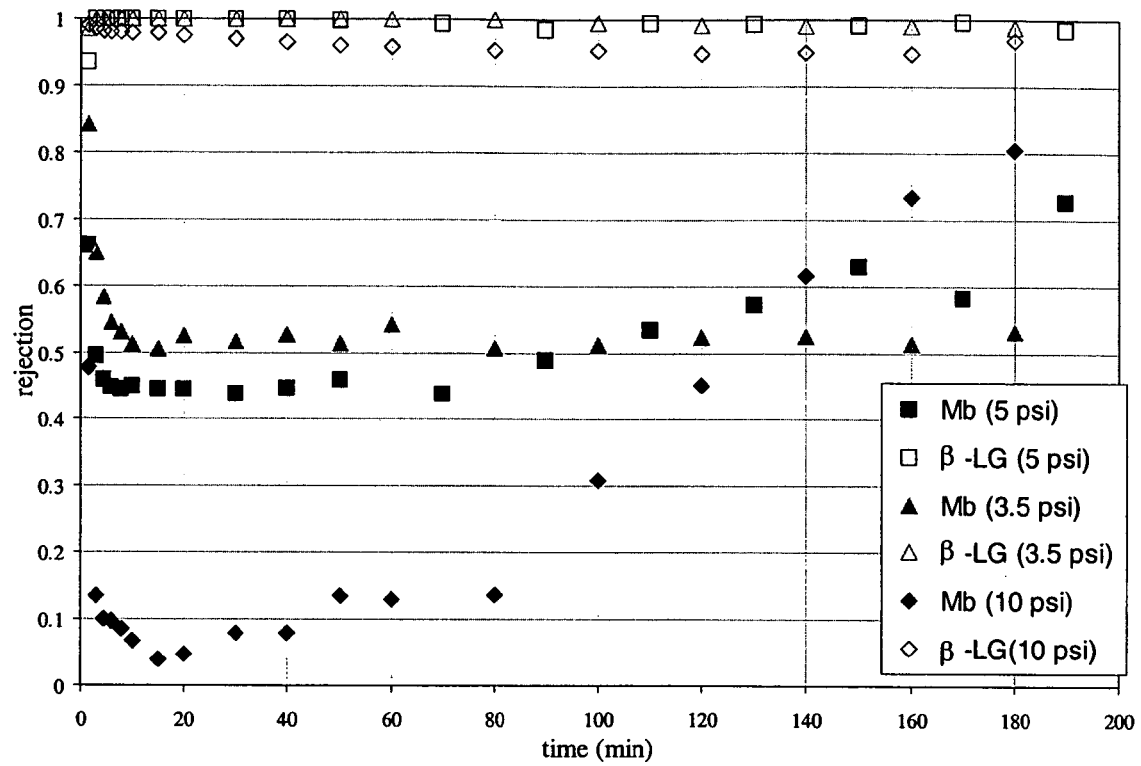
FIG. 20 is a plot of experimental rejection behaviors for an exemplary one membrane system at three different pressures according to an exemplary embodiment of the present disclosure.
Figure 21:
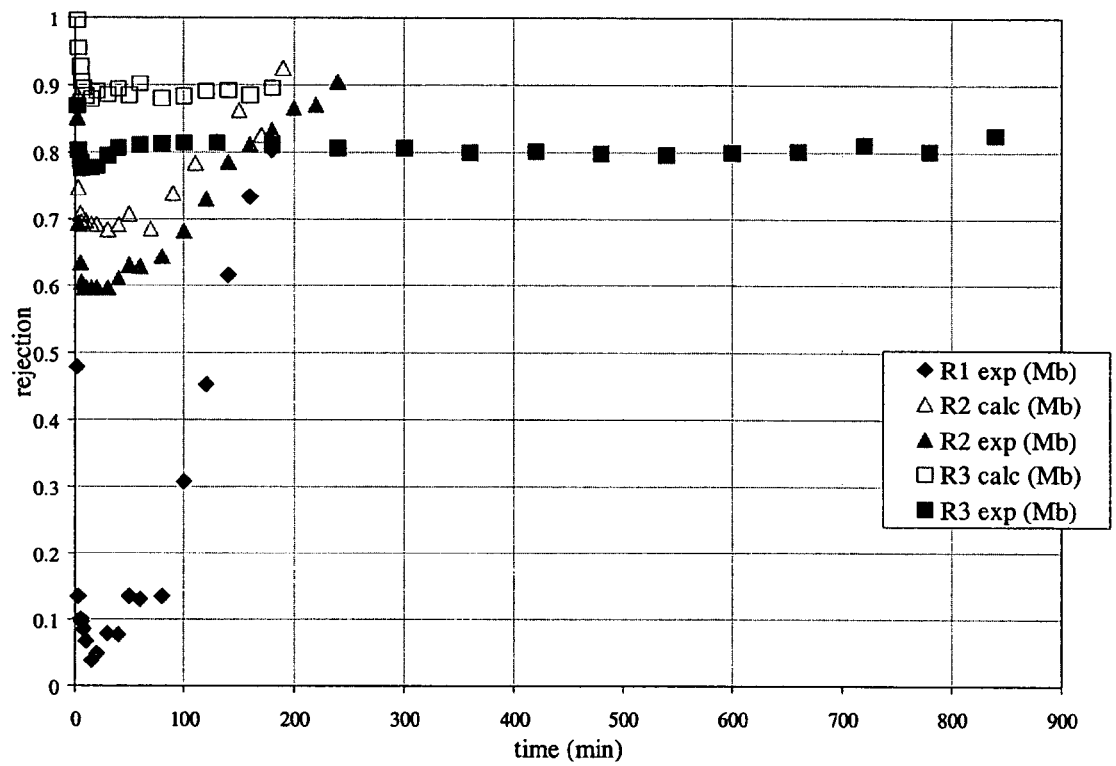
FIG. 21 is a plot of experimental and calculated rejection behaviors of myoglobin for two and three membrane systems according to an exemplary embodiment of the present disclosure.
Figure 22:
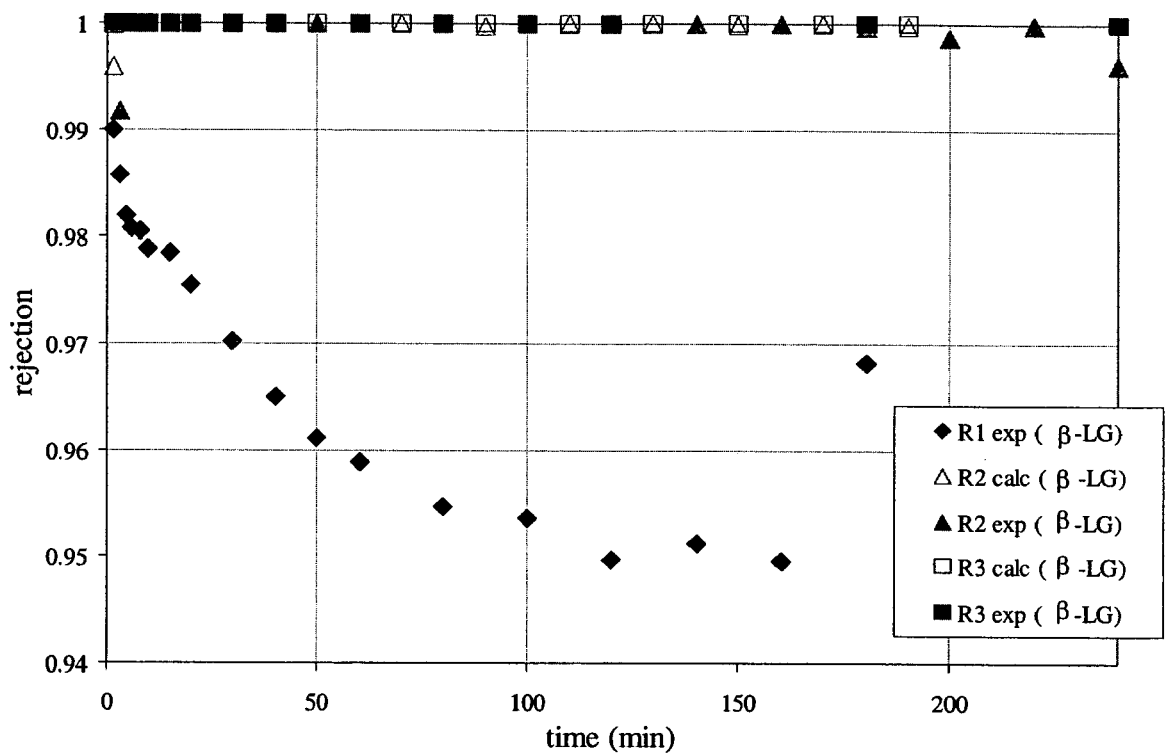
FIG. 22 is a plot of experimental and calculated rejection behaviors of β-lactoglobulin for two and three membrane systems according to an exemplary embodiment of the present disclosure.

The plot of FIG. 20 illustrates the experimental values for $R_1$ based on a single membrane system at different operating pressures. The experimental protein rejection behavior for system 1 at 10 psig is shown in the further plots of FIGS. 21 and 22 which relate to myoglobin and β-lactoglobulin, respectively, and which compare the system performances for 1, 2, and 3 membranes in series. These rejection values are compared to calculated values. When a 3 membrane composite is used, the effective pressure drop per membrane is lower. Therefore the experimental R1 values used to calculate the $R_2$ and $R_3$ for an overall pressure of 10 psig were taken from 5 and 3.3 psig for 2 and 3 membrane systems, respectively.

Figure 2:
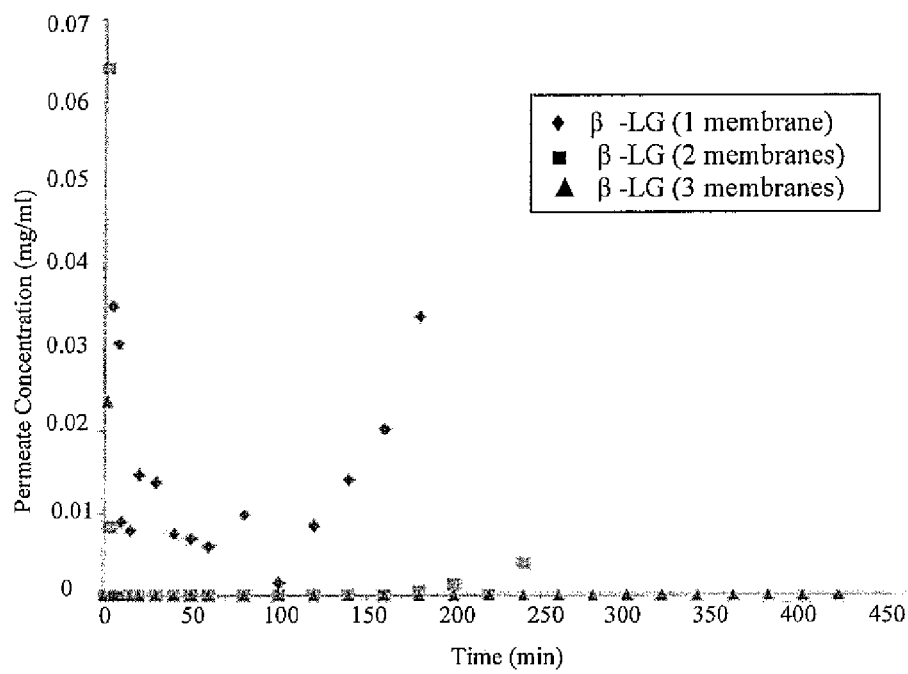
FIG. 2 is a chart of an exemplary optimized batch ultrafiltration experiment utilizing 1.0 mg/ml β-lactoglobulin (β-LG) and 0.2 mg/ml myoglobin (Mb), pH 7.3, 20 mM tris buffer, 10 psig (only more highly rejected protein, β-LG, shown).
Figure 3:
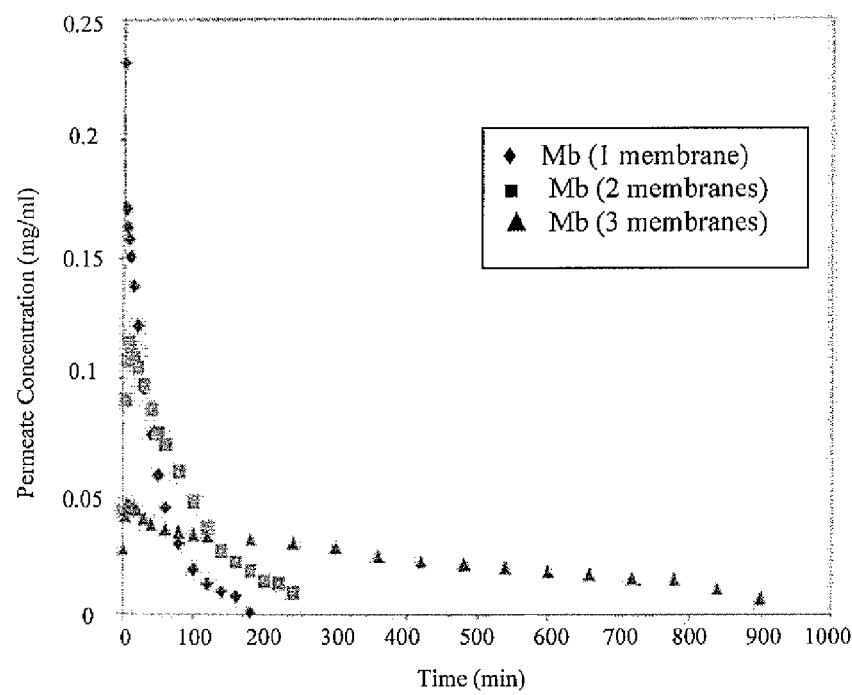
FIG. 3 is a chart of an exemplary optimized batch ultrafiltration experiment utilizing 1.0 mg/ml β-lactoglobulin (β-LG) and 0.2 mg/ml myoglobin (Mb), pH 7.3, 20 mM tris buffer, 10 psig (only permeated protein, Mb, shown).
Figure 4:
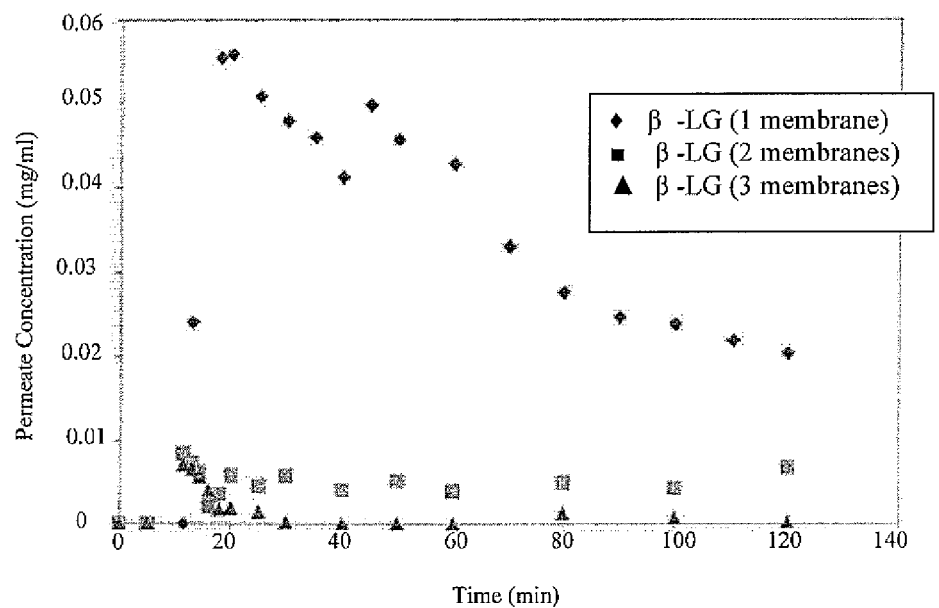
FIG. 4 is a chart of an exemplary optimized pulse injection ultrafiltration experiment utilizing 1.0 mg/ml β-lactoglobulin (β-LG) and 0.2 mg/ml myoglobin (Mb), 5 ml pulse, pH 7.3, 20 mM tris buffer, 10 psig (only more highly rejected protein, β-LG, shown).

Referring to FIG. 2, there is shown the results from experiments performed on the binary system 1 of myoglobin and β-lactoglobulin at a feed pressure of 10 psig. Here the system was operated at the pH of 7.3 (which is the pI of myoglobin) in order to fully exploit the effect of the net charges on the proteins in the mixture. The time-dependent permeate concentration profiles of β-LG are shown for each additional membrane that is added. It is shown that when 3 membranes are stacked together, we achieve essentially complete rejection of β-LG from the feed mixture, resulting in a permeate that contains Mb only. The β-LG concentration in the permeate was zero after 1.5 minutes. Amplification of a single membrane's rejection by a multimembrane composite is extraordinary. The time-dependent permeate concentrations of Mb during the same experiment are shown in FIG. 3. The percentage of myoglobin recovered in the permeate for 1, 2, and 3 membranes respectively was: 100.00%, 98.31%, and 80.25%. Results for the pulse experiments are shown in FIG. 4. Here a 5 ml pulse was introduced after 15 minutes of buffer ultrafiltration. The concentrated pulse then mixes with the buffer and results in a final concentration of 1 mg/ml β-LG and 0.2 mg/ml Mb. Other experimental conditions are the same as in FIGS. 2 and 3. It is shown that by using 3 membranes we are able to completely reject β-LG. Pulse experiments are useful when there is a small amount of valuable sample available. Also buffer conditions are controlled independently of the feed solution which allows one to operate at optimized conditions by just adjusting the buffer.

Figure 5:
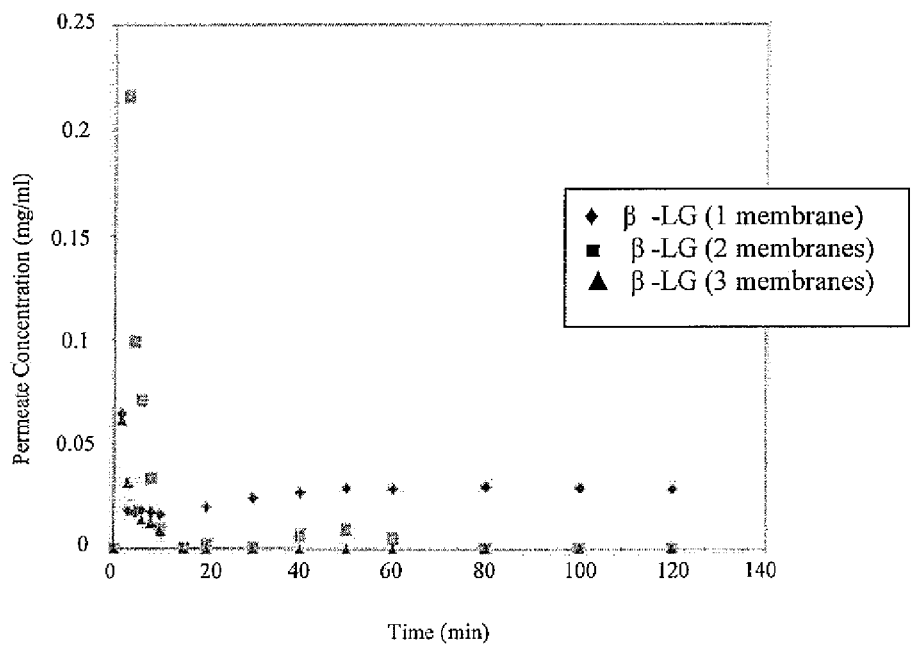
FIG. 5 is a chart of an exemplary nonoptimized batch ultrafiltration experiment utilizing 1.0 mg/ml β-lactoglobulin (β-LG) and 0.2 mg/ml myoglobin (Mb), pH 6.0, 20 mM citric acid buffer, 10 psig (only more highly rejected protein β-LG, shown).

The separation of myoglobin and β-lactoglobulin at pH 6.0 was also performed at 10 psig (FIG. 5). With the addition of each additional membrane, the concentration of β-lactoglobulin in the permeate stream was reduced, ultimately resulting in a pure myoglobin product. These results show that when operating at an arbitrary pH, one may still achieve complete fractionation with this technique. Therefore, modifications of the feed stream and buffers may be avoided which is attractive to ongoing processes.

Figure 6:
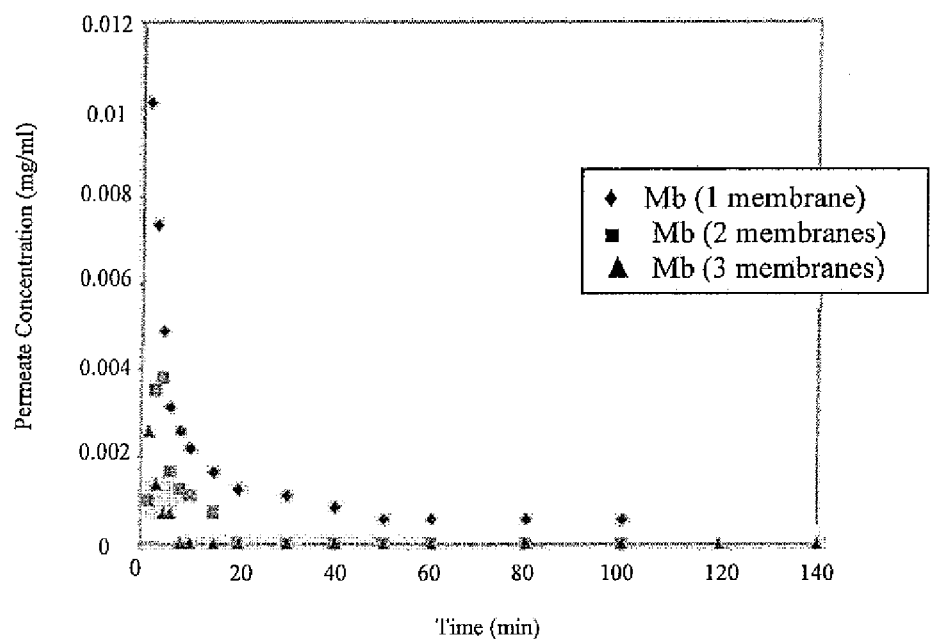
FIG. 6 is a chart of an exemplary optimized batch ultrafiltration experiment utilizing 0.2 mg/ml α-lactalbumin (α-LA) and 0.2 mg/ml myoglobin (Mb), pH 4.35, 20 mM citric acid buffer, 10 psig (only more highly rejected protein, Mb, shown).

The experimental results of system 2, α-lactalbumin and myoglobin, are shown in FIG. 6. Stacks containing 1, 2, and 3 membranes were investigated. The pH selected was 4.35 (the pI of α-lactalbumin); the operating pressure was 10 psig. Pure α-LA was obtained from the mixture after about 10 minutes of ultrafiltration with 3 membranes. Myoglobin was completely rejected. These results show that selective separation can be achieved when the molecular weight ratio of the two proteins is as low as 1.24. The results of FIG. 6 are a significant departure from the current standard range of molecular weight/size based protein fractionation via ultrafiltration.

Figure 7:
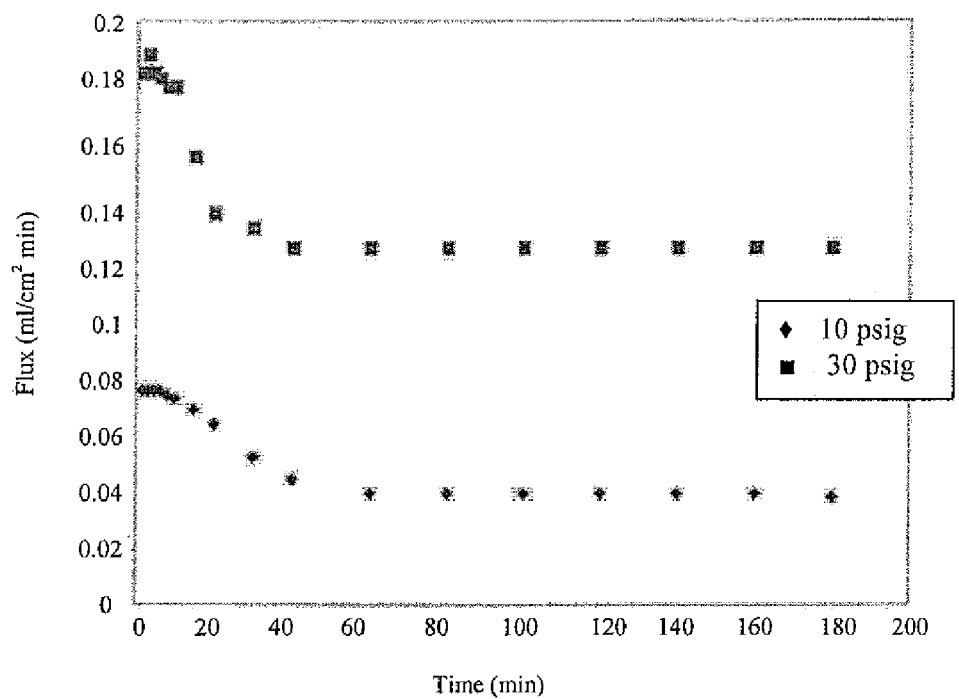
FIG. 7 is a chart of exemplary batch ultrafiltration flux measurements at two different pressures (1.0 mg/ml β-lactoglobulin (β-LG) and 0.2 mg/ml myoglobin (Mb), pH 7.3, 20 mM tris buffer, 3 membranes).
Figure 8:
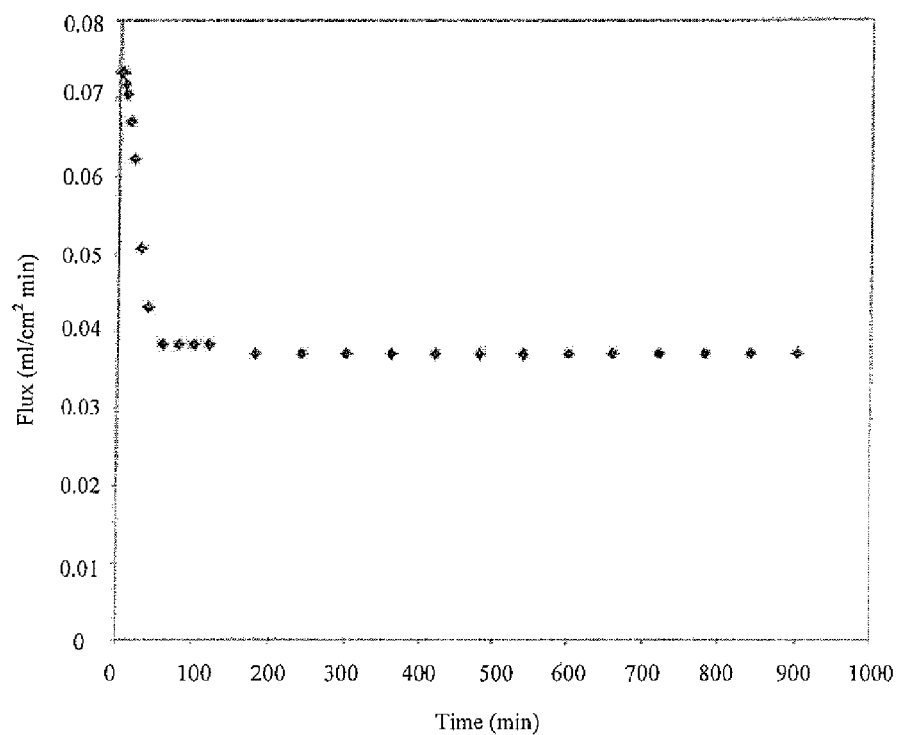
FIG. 8 is a chart of exemplary batch ultrafiltration long term flux measurements (1.0 mg/ml β-lactoglobulin (β-LG) and 0.2 mg/ml myoglobin (Mb), pH 7.3, 20 mM tris buffer, 10 psig, 3 membranes).

As one would infer, with the addition of each membrane, the ultrafiltration solvent flux in turn is reduced. We observe from FIG. 7 that by raising the pressure from 10 psig to 30 psig, we can compensate for the solvent flux loss with each added membrane while still maintaining the effectiveness of the design. Further we have seen that we can operate at steady flux levels over an extended time-period (FIG. 8). After 15 hours of operation, it is also important to note that there was no breakthrough of the unwanted protein (β-LG) (system 1). When the membranes were analyzed after completion of ultrafiltration prior to cleaning, it was found that very little protein had been adsorbed on the membranes. Less than 1.0 μg/ml of the more permeable protein was found in all cases. The more rejected protein concentration was also very low, ranging from 14 μg/ml for the top membrane to less than 1 μg/ml for the bottom membrane. This was seen under all experimental conditions.

Figure 9:
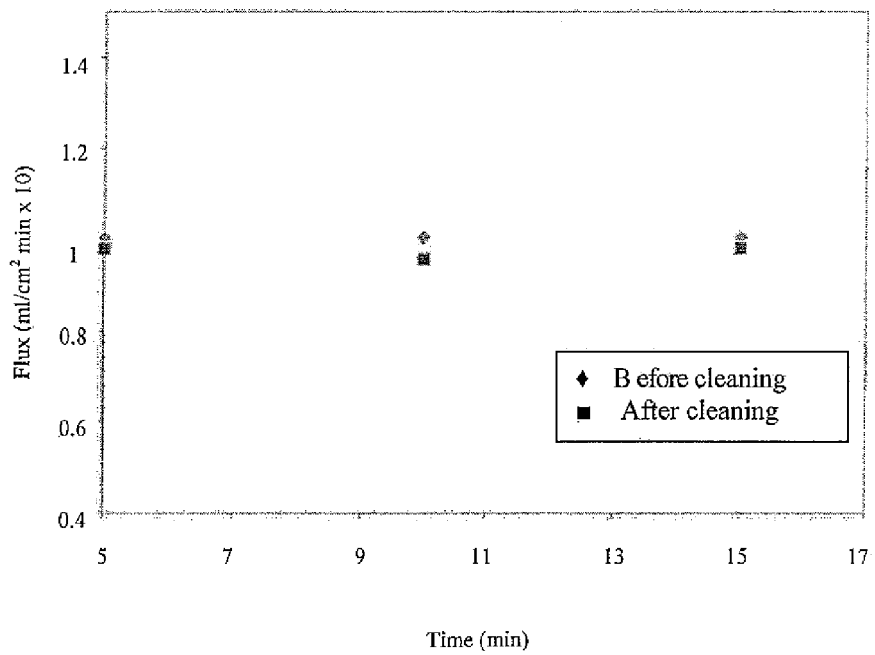
FIG. 9 is a chart of exemplary pure water flux measurements before and after cleaning in situ (10 psig, 2 membranes).
Figure 10:
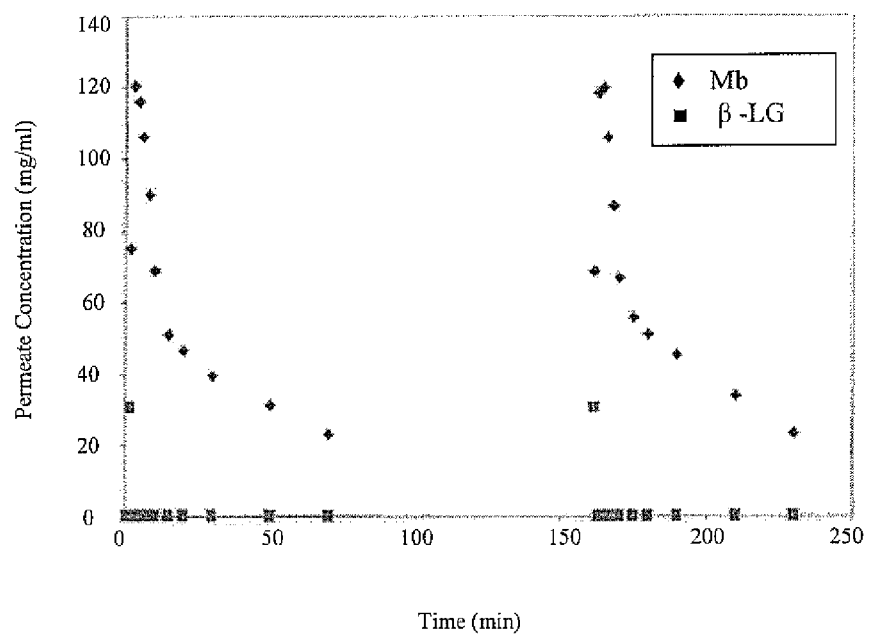
FIG. 10 is a chart of exemplary concentration profiles comparing batch ultrafiltration before and after cleaning in situ (1.0 mg/ml β-lactoglobulin and 0.2 mg/ml myoglobin, pH 7.3, 20 mM tris buffer, 30 psig, 3 membranes).

On-line cleaning of the membrane stack was performed and the results are shown in FIG. 9. We were able to recover pure water flux to within 95% of original water flux of new membranes. Our flux recovery after performing the in situ cleaning procedure was 97%. A cyclic experiment (FIG. 10) shows that the membrane composite can be cleaned in situ and the ultrafiltration behavior of the proteins observed with fresh membranes can be reproduced with the cleaned membranes. Ultrafiltration was performed with 3 membranes, then the cleaning procedure was implemented and then ultrafiltration was repeated. This means that the membrane composite can be restored to its original performance level without disassembling the apparatus. They can also be used repeatedly, which is cost effective.

Through the multimembrane composites, essentially we are creating membranes with absolute molecular weight cut-offs (MWCOs) that are unavailable commercially. When one needs a smaller MWCO membrane in order to reject a solute completely, the solvent flux can decrease considerably due to a reduction in the pore size. The multimembrane composite investigated here overcomes this problem, allows the development of customized MWCO membranes with less flux reduction than one would find by changing to a smaller MWCO membrane. Unlike chromatography, such a membrane process is continuous, scalable, easily operated, has a small footprint and is likely to be quite inexpensive.

Thus, in accordance with the foregoing illustrative first experiment, myoglobin and beta-lactoglobulin, as well as myoglobin and α-lactalbumin were studied, under various operating conditions. It is noted that the solvent flux reduction encountered when each membrane is added may be avoided, by operating at increased pressure, while still achieving the desired purification. It is also noted that cleaning in situ can be achieved with reproducible experimental results before and after on-line cleaning. In sum, the results clearly demonstrate that multimembrane stacks can be used for fractionation of proteins that are substantially close in molecular weight/size.

To further illustrate the benefits associated with the technique for obtaining protein from a binary protein mixture by utilizing membranes in series, the following additional illustrative experiment was performed using:

Hemoglobin (Hb, MW 64677; Dickerson R E, Geis I, *The Structure and Action of Proteins*. Harper and Row, Publisher, New York, pp 5321, 1969), and Bovine serum albumin (BSA, MW 66430; Hirayama K, Akashi S, Furuya M, Fukuharak, *Rapid Confirmation and Revision of The Primary Structure of Bovine Serum Albumin by Esims and Frit-Fab LC/MS*, Biochemical and Biophysical Research Communications, 173:639-646, 1990).

Both of the noted proteins were purchased from Sigma (St. Louis, Mo.).

The pI values for Hb, and BSA are, respectively, 6.8 [Lehninger, Biochemistry. $2^{nd}$ Ed. Worth Publisher, New York, pp 162, 1975] and 4.7 [Longsworth L G, Jacobsen C F, *An*

*electrophoretic study of the binding of salt ion by β-lactoglobulin and bovine serum albumin*, J Phys. Colloid Chem 53:126-135, 1949]. 20 mM sodium phosphate buffer at pH 6.8 and 2.3 mM sodium phosphate buffer at pH 6.8.

Similar to the illustrative experiments previously discussed, protein solutions for use in this additional illustrative experiment were prepared by dissolving the desired protein in the appropriate buffer solution at room temperature. Buffer solutions were prefiltered through a 0.45 µm pore size Durapore membrane (Millipore, Bedford, Mass.) prior to use. The protein solutions were then prefiltered through 0.45 µm pore size Durapore membranes (Millipore) to remove any undissolved proteins and large particulates. Protein solutions were stored at 4° C. and used within 24 hours in order to ensure no bacterial contamination. Also, the protein concentrations in the mixture were determined by the dual-wavelength method using a Hitachi U-2000 (Danbury, Conn.) UV-VIS spectrophotometer at 407 nm and 280 nm.

The employed set-up in accordance with the second illustrative experiment is as shown in FIG. 1 [Sirkar K K, Prasad R, *Protein ultrafiltration—some neglected considerations*, In McGregor W C editor, Membrane Separations in Biotechnology, New York: Marcel Dekker, pp 37-59, 1986]. Regenerated cellulose flat membrane disks (YM100, MWCO 100, 000, diameter 76 mm) from Millipore (Bedford, Mass.) and polyethersulfone flat membrane disks (MWCO 100,000) from Pall Corporation (East Hills, N.Y.) were chosen for this experiment.

Similar to the previously described experiments, prior to use, the membranes were soaked overnight in protein solution to equilibrate the membranes prior to ultrafiltration. Likewise, all filtration experimental iterations were conducted using the 76 mm stirred ultrafiltration cell (model 8400, Amicon Corporation) 120 and the two solvent reservoirs 130, 140. Further, one buffer reservoir 130 of stainless steel was filled with a pure specific buffer of an appropriate pH while the other acrylic reservoir 140 contained cleaning solution or was left empty for steady state experiments. In addition, all of the above were batch ultrafiltration experiments with fresh buffer replacing the lost solvent volume.

As was done in the previously described experiments, preliminary experiments on single membrane studies were conducted with a binary protein mixture. These preliminary experiments were operated at different pressures to explore the rejection characteristics encountered in-between the membrane stack where concentrations cannot be measured directly and more membranes were added to illustrate the changing rejection behavior. Membranes of a determined number were stacked together without any adhesive or spacer in-between them. Fractions were collected at timed intervals and the permeate flow rate was measured using timed collections. All experiments were conducted at constant pressure and were performed at room temperature (22±2° C.).

Occasionally after ultrafiltration experiments were completed, the membranes were, as with the first experiment, soaked in deionized water overnight (prior to cleaning). The water solution was then analyzed to measure the amount of protein that was desorbed from the membrane.

With respect to cleaning operations, after completion of the experiments, cleaning was conducted, as in the first experiment, in two ways: in situ or off-line. Off-line cleaning procedures required disassembling the apparatus and briefly rinsing the membranes 110 with tap water. Then, separately, 0.1 M NaOH was passed through the membrane for approximately 45 minutes and deionized water was subsequently passed through the membrane and the pure water flux was monitored. The integrity and performance of the membrane are maintained if this flux is within at least 95% of the virgin membrane's pure water flux. Whereas, in situ cleaning was done by allowing the feed solution to completely exit the ultrafiltration cell 120. The second reservoir 140 was filled with 0.5 M NaOH at 45° C. and this solution was allowed to permeate through the membranes. Then, diafiltration was turned off, as the system was operating in dead-end filtration mode. The total time of exposure was between 45 minutes and 1 hour (which is according to the manufacturer's specifications). Deionized water, from the second reservoir 140, was then allowed to pass through the system for one hour. The pure water flux was monitored. The membranes were stored in 0.05 sodium azide/water solution at 4° C.

Results and Discussion

The solute rejection, $R_1$, for the first membrane as well as a single membrane for a solute is given by equation (1) previously identified/discussed above with respect to the first experiment. Further, as with the first experiment, the rejection for a two-membrane system may be calculated by rearranging equation (1) and assuming a rejection value valid for a single membrane system to generate equations (2a) to (2e). Likewise, the overall rejections $R_2$, $R_3$ respectively for the systems of two membranes and three membranes in series can be defined by equations (3) through (6) previously identified/discussed with respect to the first experiment. As previously noted, these relationships illustrate how high the rejection can be when it is amplified with each additional membrane.

Figure 11:
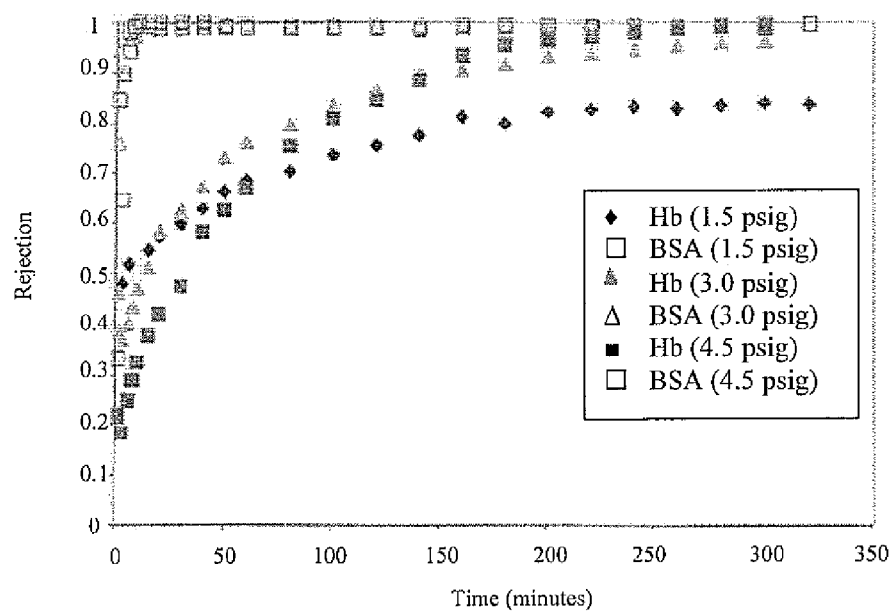
FIG. 11 is a chart of exemplary experimental rejection behaviors for one membrane at three different pressures (batch ultrafiltration: 1.0 mg/ml bovine serum albumin (BSA) and 0.2 mg/ml hemoglobin (Hb). pH 6.8, 2.3 mM sodium phosphate buffer; Omega 100K membranes, 1.5, 3, and 4.5 psig).
Figure 12:
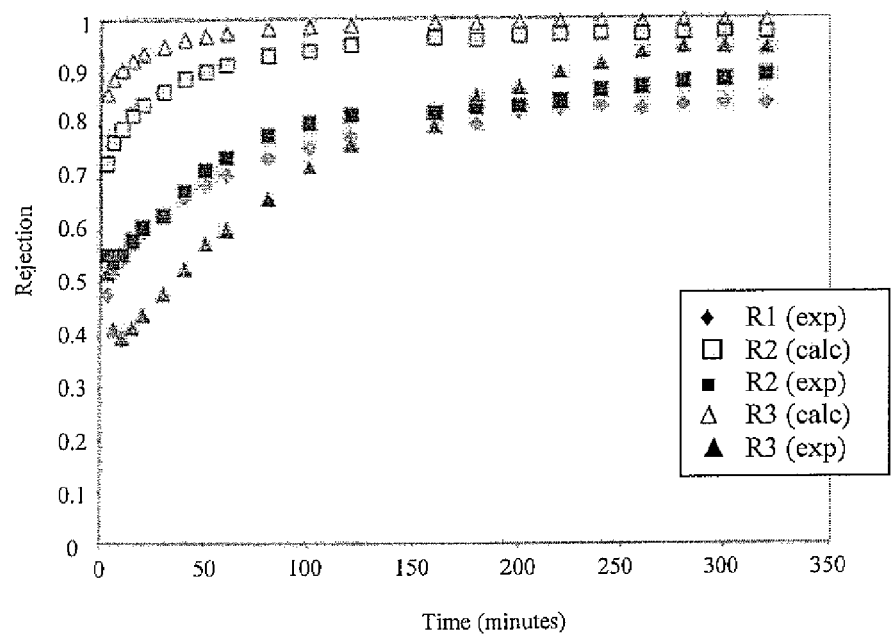
FIG. 12 is a chart of exemplary experimental and calculated rejection behaviors of hemoglobin for 1, 2 and 3 membranes systems (batch ultrafiltration: 1.0 mg/ml bovine serum albumin and 0.2 mg/ml hemoglobin, pH 6.8, 2.3 mM sodium phosphate, Omega 100K membranes, 1.5, 3, and 4.5 psig).
Figure 13:
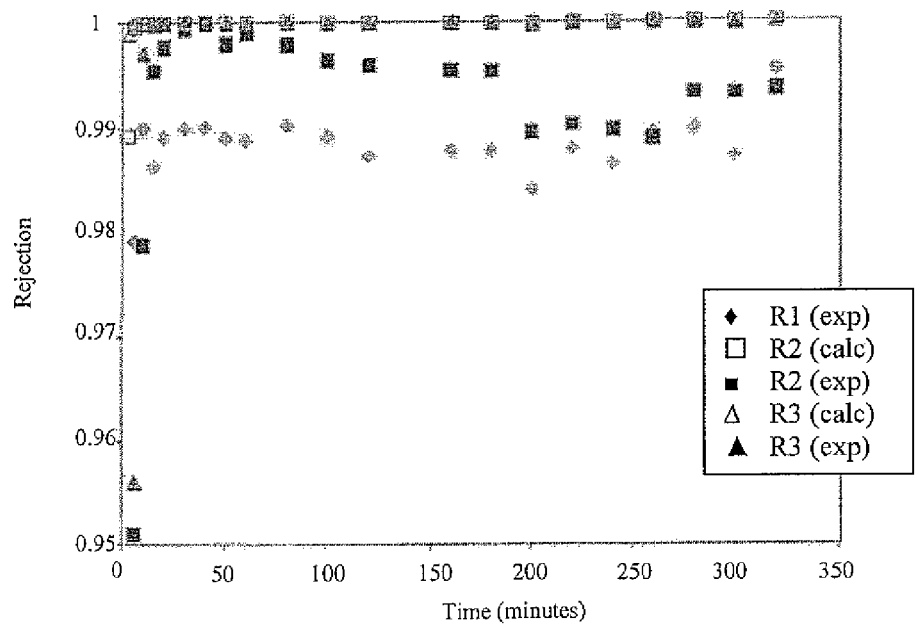
FIG. 13 is a chart of exemplary experimental and calculated rejection behaviors of bovine serum albumin (BSA) for 1, 2 and 3 membrane systems (batch ultrafiltration: 1.0 mg/ml bovine serum albumin (BSA) and 0.2 mg/ml hemoglobin (Hb), pH 6.8, 2.3 mM sodium phosphate buffer; Omega 100K membranes, 1.5, 3, and 4.5 psig).

FIG. 11 illustrates the experimental values of $R_1$ based on a single Omega 100K membrane system for the two proteins at three different operating pressures (4.5. 3, and 1.5 psig) and pH 6.8. The experimental protein rejection behaviors at 4.5, 3, and 1.5 psig and pH 6.8 for hemoglobin and bovine serum albumin are shown respectively in FIG. 12 and FIG. 13, comparing the system performances for 1, 2, and 3 Omega 100K membranes in series. These observed rejection values are compared to calculated values from equations 5 and 6 for 2 and 3 membranes in series. When a 2 or 3 membrane composite is used, the effective pressure drop per membrane is lower. Therefore the experimental $R_1$ values from 1.5 psig data were used to calculate the $R_2$ for an overall feed pressure of 3 psig for a 2-membrane composite. $R_1$ values from 1.5 psig data were used to calculate the $R_2$ and $R_3$ for an overall pressure of 4.5 psig for a 3 membrane composite.

The values of experimental and calculated values of rejections are not identical in FIG. 12. The values of $R_1$ used for calculation correspond to a certain level of concentration polarization in the feed due to particular mixing conditions in the cell in the single membrane. The mixing conditions on top of the second membrane and the third membrane in the 2-membrane and 3-membrane composites are different; we have stagnant conditions which lead to lower rejections. Therefore, the experimentally observed $R_2$ and $R_3$ values are lower than the calculated values shown in FIG. 12. Our objective here, however, was to test the crude model based on the concept of rejection amplification. It appears to provide a good guidance toward the observed rejection increase. More detailed modeling using stagnant conditions in the space between two continuous membranes in the stack is quite likely to be useful. However, the conditions in and the dimensions of the inter-membrane space are unknown.

Figure 14:
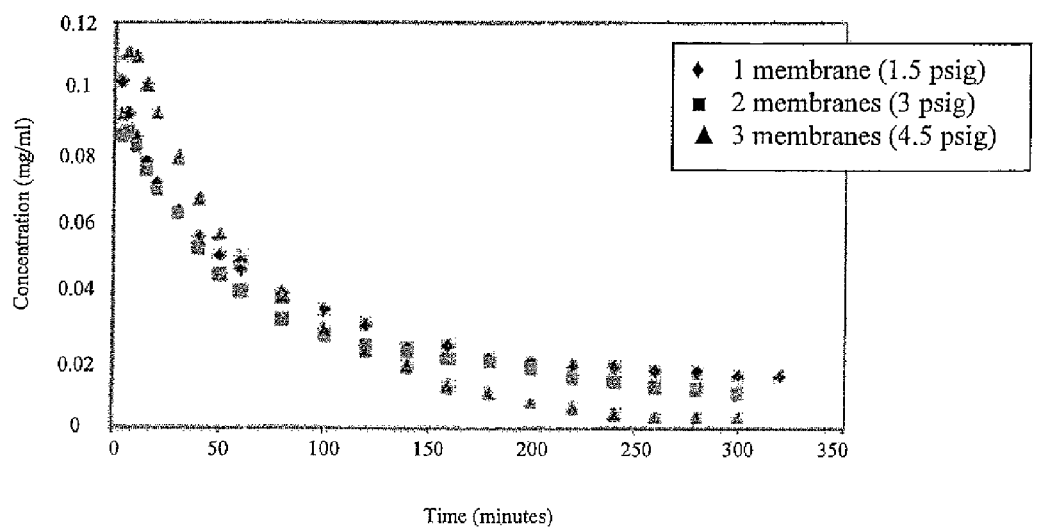
FIG. 14 is a chart of an exemplary optimized batch ultrafiltration utilizing 1.0 mg/ml bovine serum albumin (BSA) and 0.2 mg/ml hemoglobin (Hb), pH 6.8, 2.3 mM sodium phosphate buffer; Omega 100K membranes, 1.5, 3, and 4.5 psig (only permeated protein, hemoglobin (Hb), shown).
Figure 15:
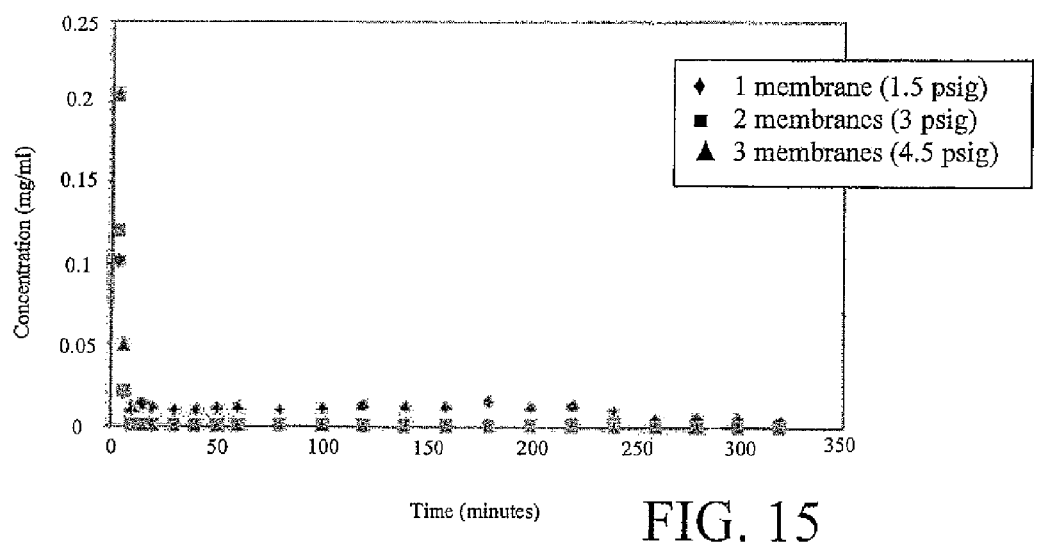
FIG. 15 is a chart of an exemplary optimized batch ultrafiltration utilizing 1.0 mg/ml bovine serum albumin (BSA) and 0.2 mg/ml hemoglobin (Hb), pH 6.8, 2.3 mM sodium phosphate buffer; Omega 100K membranes, 1.5, 3, and 4.5 psig (only more highly rejected protein, bovine serum albumin (BSA), shown).

The separation of hemoglobin and bovine serum albumin at 2.3 mM, pH 6.8 was performed at 1.5, 3, and 4.5 psig (FIG. 14 and FIG. 15) using an Omega 100K polyethersulfone membrane. The time-dependent permeate concentration profiles of the more permeable protein, hemoglobin, are shown in FIG. 14 for each additional membrane that is added; FIG. 15 shows those for BSA. It is shown that when 3 membranes are stacked together, we achieve essentially complete rejection of bovine serum albumin from the feed mixture, resulting in a permeate that contains hemoglobin only. These results, for this particular system, show that when low ionic strength and pH=pI of the protein of interest are maintained, complete fractionation is achieved with this technique. The bovine serum albumin concentration in the permeate was zero after 10 minutes. Amplification of a single membrane's rejection by a multimembrane composite is extraordinary. The time-dependent permeate concentrations of hemoglobin during the same experiment are shown in FIG. 14. The percentages of hemoglobin recovered in the permeate during the experimental duration of 300 minutes for 1, 2, and 3 membranes respectively were: 55.44%, 50.92%, and 60.60%. Longer time for the 3-membrane system would have led to almost complete hemoglobin recovery.

Figure 16:
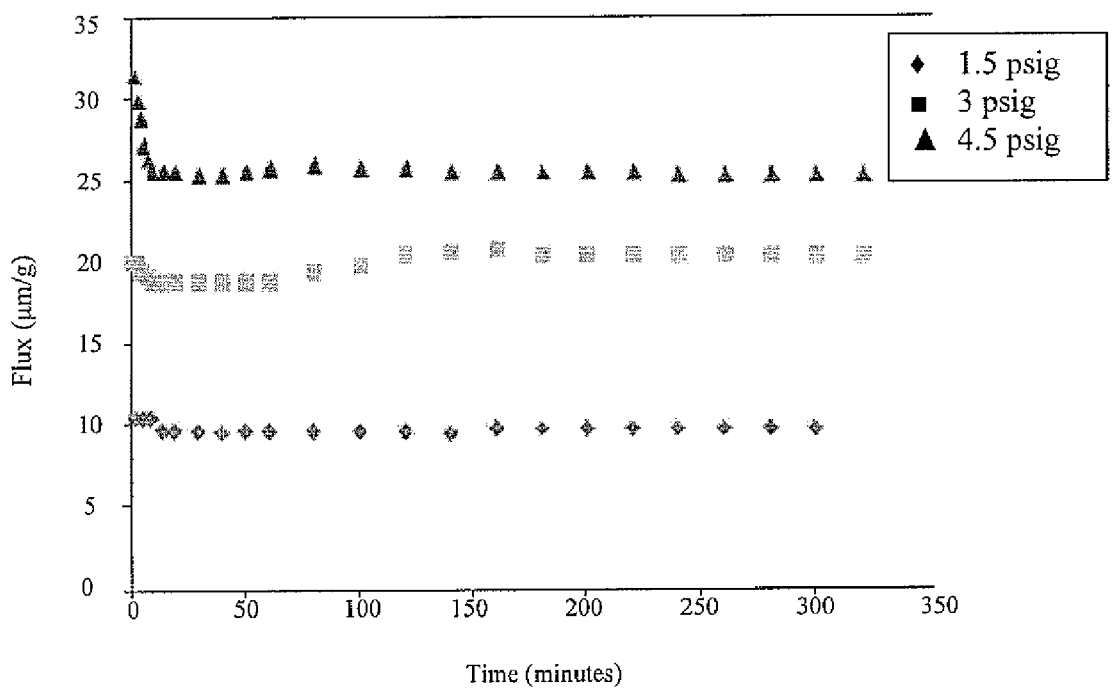
FIG. 16 is a chart of exemplary batch ultrafiltration flux measurements of 1, 2- and 3-membrane composites at three different pressures (1.0 mg/ml bovine serum albumin (BSA) and 0.2 mg/ml hemoglobin (Hb), pH 6.8, 2.3 mM sodium phosphate buffer; Omega 100K membranes, 1.5, 3, and 4.5 psig).

By operating at increasing pressure with each additional membrane, the flux loss is also recovered. The flux profiles observed during the above described conditions are shown in FIG. 16. This figure illustrates that the system operates at steady flux, disregarding the first 10-15 minutes of unsteady behavior due to system equilibration. It is also important to note that when operating at 4.5 psi, there is more evidence of flux decline due to increased concentration polarization. However, we can still overcome the overall loss of flux that is encountered with a 3-membrane composite by raising the pressure. After 5 hours of operation, it is also important to note that there was no breakthrough of the unwanted protein (BSA).

Experiments were performed on two different membranes and investigated using two different ionic strengths of the buffer. As described in connection with the prior experiments, separations using stacked membranes may not need to be optimized, but in this system buffer optimization and membrane selection were important to achieve complete purification. Using the polyethersulfone Omega 100K membrane at an ionic strength 2.3 mM, our technique was successful. Selectivity can be used to evaluate the experimental data and is defined as:

$$\Psi = [c_{fHb}/c_{fBSA}]/[c_{pHb}/c_{pBSA}] \quad (7)$$

Figure 17:
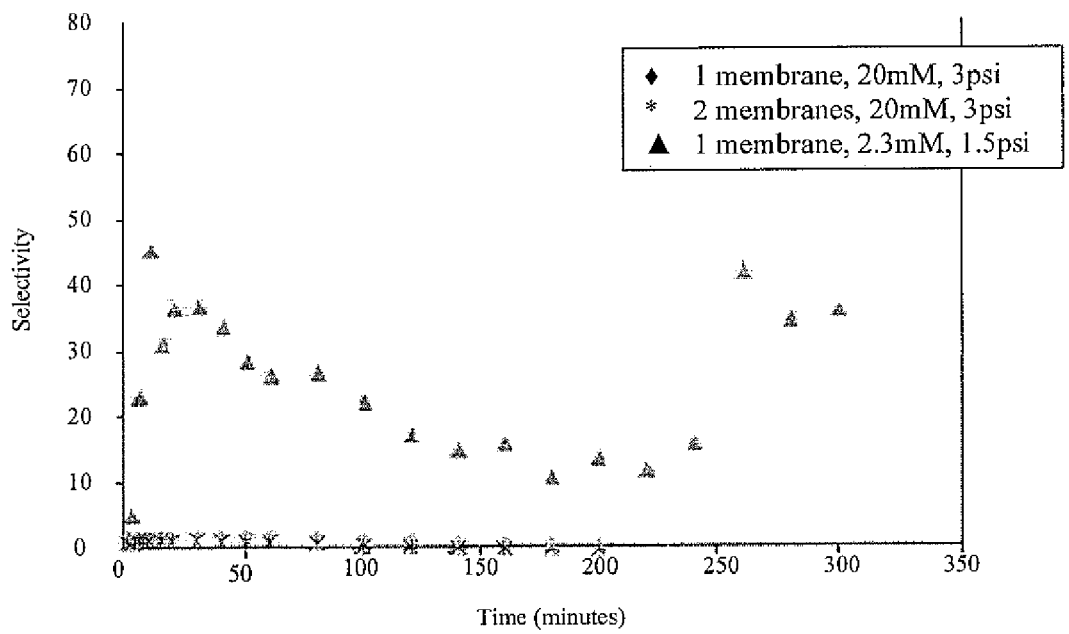
FIG. 17 is a chart of exemplary selectivities comparing ionic strengths for Omega 100K ultrafiltration membranes (1.0 mg/ml bovine serum albumin (BSA) and 0.2 mg/ml hemoglobin (Hb), pH 6.8, 2.3 mM and 20 mM sodium phosphate buffer; 1.5 psig and 3.0 psig).

Notation $c_{fBSA}$ concentration of BSA on the feed side of single membrane of stack, μg/ml $c_{fHb}$ concentration of hemoglobin on the feed side of single membrane of stack, μg/ml $C_{pBSA}$ concentration of BSA in the final permeate, μg/ml $c_{pHb}$ concentration of hemoglobin in the final permeate, μg/ml $\Psi$ selectivity FIG. 17 shows the selectivity data of Omega 100K membranes at 2 different ionic strengths and pressures. No significant selectivity was observed at 20 mM buffer concentration when investigating a single membrane system or a 2-membrane composite.

Figure 18:
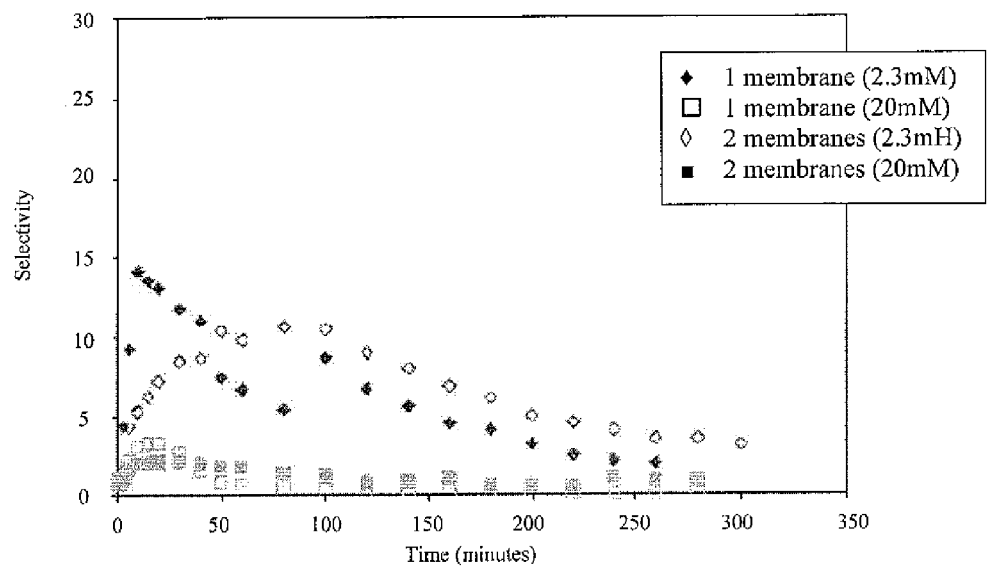
FIG. 18 is a chart of exemplary selectivities comparing ionic strengths for YM100 ultrafiltration membranes (1.0 mg/ml bovine serum albumin (BSA) and 0.2 mg/ml hemoglobin (Hb), pH 6.8, 2.3 mM and 20 mM sodium phosphate buffer; 1.5 psig and 3.0 psig).

Low selectivity was observed when using the YM100 regenerated cellulose membranes regardless of the buffer conditions or operating pressures. FIG. 18 shows the selectivity for 1 and 2 membranes under two different buffer conditions. Selectivities ranged from 0-2 when operating at 20 mM ionic strength buffer and was not amplified when the membrane number was increased. At lower ionic strengths (2.3 mM), selectivities were slightly higher (0-14) but sufficient selectivity enhancement was not observed when a 2-membrane composite was investigated. These data reveal that high selectivities (as seen in FIG. 17) must be attained in single membrane systems in order to have complete rejection in a multiple membrane systems of 3 or more membranes.

An extensive study of buffer effects on the zeta potential of ultrafiltration membranes has been conducted [Burns, D B, Zydney A L, *Buffer effects on the zeta potential of ultrafiltration membranes*, J Membr. Sci 172:39-48, 2000]. Due to a diffuse double layer of ions present near the surface of the membrane, ionic strength and membrane charge are important variables in separation. Operating at low ionic strength creates a more diffuse double layer due to the lack of ions present to adsorb on the membrane surface. Therefore, at low ionic strengths there is more repulsion from the negatively charged BSA and the negatively charged membrane surface. Burns and Zydney [2000] presented limited data for the Omega 100K membrane and showed at pH 6.8, the apparent zeta potential was at a minimum with a value of approximately −17.0 (mV). Regenerated cellulose YM100 was found to have a zeta potential of around −4.5 mV [Kim K J, Fane A G, Nystrom M, Pihlajamaki A, Bowen W R, Mukhtar H, *Evaluation of electroosmosis and streaming potential for measurement of electrical charges of polymetric membranes*, J Membr. Sci 116:149-159, 1996] at pH 6.8, which therefore explains the reason for increased rejection of BSA by the Omega 100K membrane. This explains the increased selectivity obtained with this binary system at 2.3 mM (FIG. 16) using the polyethersulfone membrane. Therefore, when purifying mixtures of similar molecular weight, membrane selection is an important consideration. When the membranes were analyzed after completion of ultrafiltration prior to cleaning, it was found that very little protein had been adsorbed on the membranes on the YM100 membranes, while more significant amounts were seen on the Omega 100K membranes. In the case of the YM100 membranes, less than 7.0 μg/ml of the more permeable protein was found in all cases. The more rejected protein concentration was also very low, ranging from 33 μg/ml for the top membrane to less than 25 μg/ml for the bottom membrane. In the case of the Omega 100K membranes, less than 25.0 μg/ml of the more permeable protein was found in all cases. The more rejected protein concentration was, ranging from as high as 582 μg/ml for the top membrane to 333 μg/ml for the bottom membrane.

On-line cleaning of the membrane stack was performed and the results are shown in Table 1 below.

TABLE 1

| Virgin membrane water flux (μm/s) | After cleaning water flux flux (μm/s) | Percent recovery of original flux (%) |
|---|---|---|
| 30.16 | 29.30 | 97.06 |

Figure 19:
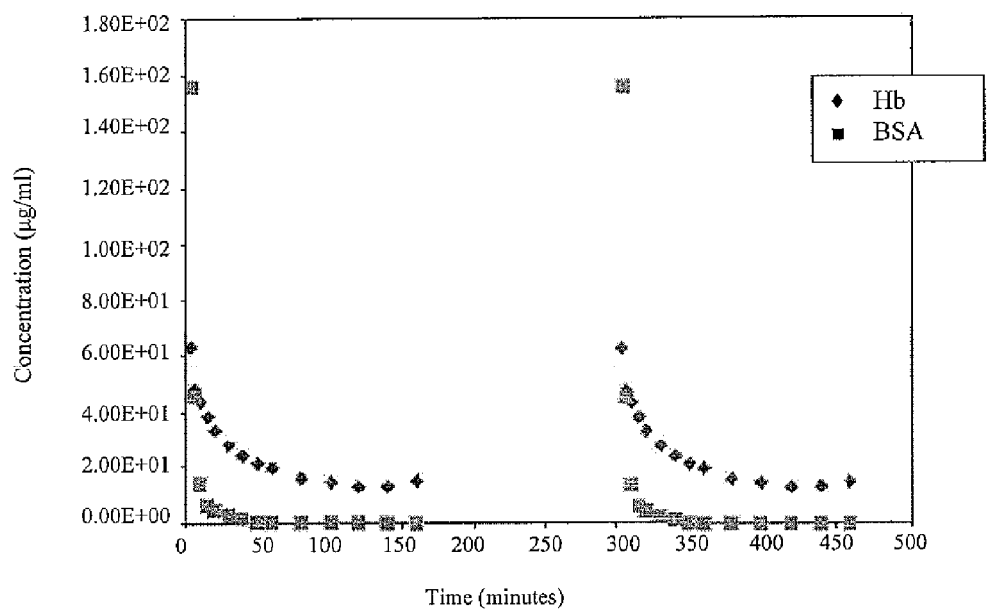
FIG. 19 is a chart of exemplary concentration profiles versus time comparing batch ultrafiltration before and after cleaning in situ (1.0 mg/ml bovine serum albumin (BSA) and 0.2 mg/ml hemoglobin (Hb), pH 6.8, 2.3 mM sodium phosphate buffer; 3 Omega 100K membranes, 4.5 psig).

We were able to recover pure water flux to within at least 95% of original water flux of new membranes. Our flux recovery after performing the in situ cleaning procedure was 97%. A cyclic experiment (FIG. 19) shows that the membrane composite can be cleaned in situ and the ultrafiltration behavior of the proteins observed with fresh membranes can be reproduced with the cleaned membranes. Ultrafiltration was performed with three membranes, then the cleaning procedure was implemented and then ultrafiltration was repeated. This means that the membrane composite can be restored to its original performance level without disassembling the apparatus. They can also be used repeatedly, which is cost effective.

It is also useful to determine the yield versus diavolumes for a given binary mixture in the multimembrane composite system. In view of our previous comments on the limited extent of flux reduction in a multimembrane composite, we have calculated the hemoglobin yield from our data for 1 membrane, 2-membrane composite, and a 3-membrane composite. From Table 2 below, we note that the 2-membrane composite and the 3-membrane composite require about 1.3-1.4 times the diavolumes required for a single membrane.

TABLE 2

|  | Hemoglobin yield (%) | Number of diavolumes | Time (minutes) |
|---|---|---|---|
| 1 membrane (1.5 psig) | 56.49 | 3.16 | 280* |
| 2 membranes (3 psig) | 50.92 | 3.41 | 300* |
| 3 membranes (4.5 psig) | 60.64 | 4.45 | 300* |

*Longer period of operation needed for complete recovery

The very small membrane area used in our cell leads to apparently a very long processing time. This should be of no consequence in practical ultrafiltration where membrane area facing the feed liquid may be easily increased.

Through the multimembrane composites, essentially we are creating membranes with absolute molecular weight cut-offs (MWCOs) that are unavailable commercially. A multi-membrane stack potentially develops a much sharper pore size distribution. When one needs a smaller MWCO membrane in order to reject a solute completely, the solvent flux can decrease considerably due to a reduction in the pore size since the solvent flux is proportional to the fourth power of the pore diameter. The multimembrane composite investigated here overcomes this problem, allows the development of customized MWCO membranes with less flux reduction than one would find by changing to a smaller MWCO membrane. For example, when switching to the next available smaller size regenerated polyethersulfone membrane (Omega 50K) having a MWCO of 50,000, the flux will be reduced as much as six (6) times (according to data provided by manufacturer) without a guarantee of complete rejection. The flux reduction in a multimembrane stack for Omega 100K membrane is only two (2) times lower for two membranes, three times lower for three membranes, etc. (which we can overcome by increasing the pressure two times for two membranes and three times for three membranes). Yet the selectivity enhancement is extraordinary. Unlike chromatography, such a membrane process is continuous, scalable, easily operated, has a small footprint and is likely to be quite inexpensive. Moreover, the membrane systems and techniques of the present disclosure may be advantageously employed for the separation and purification of a wide range of biomolecules, including polysaccharides.

The references cited in the specification are incorporated herein by reference to the extent that they supplement, explain, provide a background for or teach methodology, techniques and/or compositions employed herein.

Although the advantageous system and method of the present disclosure have been described with reference to exemplary embodiments thereof, the present disclosure is not limited to or by such exemplary embodiments; rather, the systems and methods of the present disclosure may be employed in alternative ways, in alternative modalities, and/or to achieve alternative results. Thus, the present disclosure encompasses alternative implementations, as will be apparent to persons skilled in the art from the description provided herein, and such alternative implementations, whether enhancements, modifications and/or variations, are within the spirit and scope of the disclosed invention.

What is claimed is:

1. A method for obtaining purified proteins, comprising:
   a) providing a first, a second, and a third ultrafiltration membrane with each membrane having the same, or substantially the same, molecular weight cut-off, wherein the first, second and third ultrafiltration membranes are stacked together in an unspaced arrangement and are positioned in series;
   b) supplying a multi-component protein mixture to the first, second and third stacked ultrafiltration membranes, the multi-component protein mixture having at least (i) a first protein and (ii) a second protein; and
   c) employing ultrafiltration at the first, second and third stacked ultrafiltration membranes to separate the first protein from the second protein;
   wherein each ultrafiltration membrane is configured to only partially reject the second protein without the other two ultrafiltration membranes being present;
   wherein the first, second and third stacked ultrafiltration membranes reject the second protein resulting in generation of a substantially pure first protein permeate; and
   wherein the operative conditions associated with the first, second and third stacked ultrafiltration membranes are controlled so as to generate the substantially pure first protein permeate.

2. The method according to claim 1, wherein said operative conditions are controlled so as to optimize at least one of the following parameters for selectivity: feed conditions, pH, membrane selection, and membrane charge.

3. The method according to claim 1, wherein said ultrafiltration membranes are selected from the group consisting of cellulose membranes, polyethersulfone membranes, combinations of cellulose and polyethersulfone membranes, and membranes fabricated from another ultrafiltration material.

4. The method according to claim 1, wherein the molecular weight cutoff(MWCO) of adjacent membranes differ by no more than about 10 to 20% for membranes having a MWCO of greater than about 50,000.

5. The method of claim 1, wherein the molecular weight cutoff (MWCO) of adjacent membranes differ by no more than about 25% for membranes having a MWCO of less than about 50,000.

6. The method of claim 1, wherein the molecular weights ratio of the first protein and the second protein is about 1.03.

7. The method of claim 1, wherein the molecular weight ratio of the first protein and the second protein is about 1.24.

8. The method of claim 1, wherein the multi-component protein mixture further comprises a third protein and during step c the first protein is separated from the second protein and the third protein to generate (i) a substantially pure first protein permeate and (ii) a retentate containing the second protein and the third protein;
   wherein after the operative conditions associated with the first, second and third stacked ultrafiltration membranes are controlled so as to generate the substantially pure first protein permeate and after the substantially pure first protein permeate is generated, the operative conditions associated with the first, second and third ultrafiltration membranes are adjusted so as to generate a substantially pure second protein permeate; and
   wherein the method further includes the steps of:
   d) supplying the retentate containing the second and third proteins to the first, second and third stacked ultrafiltration membranes;
   e) employing ultrafiltration at the first, second and third stacked ultrafiltration membranes to separate the second protein from the third protein, wherein the first, second and third ultrafiltration membranes reject the third protein resulting in generation of a substantially pure second protein permeate.

9. The method of claim 1, wherein the multi-component protein mixture further comprises a third protein and during step c the first protein is separated from the second protein and the third protein to generate (i) a substantially pure first protein permeate and (ii) a retentate containing the second protein and the third protein;

wherein after the operative conditions associated with the first, second and third stacked ultrafiltration membranes are controlled so as to generate the substantially pure first protein permeate and after the substantially pure first protein permeate is generated, the method further includes the steps of:

d) providing a fourth, a fifth and sixth ultrafiltration membrane with each membrane having the same, or substantially the same, molecular weight cut-off, wherein the fourth, fifth and sixth ultrafiltration membranes are stacked together in an unspaced arrangement and are positioned in series;

e) supplying the retentate containing the second and third proteins to the fourth, fifth and sixth stacked ultrafiltration membranes;

f) employing ultrafiltration at the fourth, fifth and sixth stacked ultrafiltration membranes to separate the second protein from the third protein, wherein the fourth, fifth and sixth ultrafiltration membranes reject the third protein resulting in generation of a substantially pure second protein permeate;

wherein each of the fourth, fifth and sixth membrane is configured to only partially reject the third protein without the other two ultrafiltration membranes being present; and wherein the operative conditions associated with the fourth, fifth and sixth stacked ultrafiltration membranes are controlled so as to generate the substantially pure second protein permeate.

* * * * *